(12) United States Patent
Anderson

(10) Patent No.: US 8,609,385 B2
(45) Date of Patent: Dec. 17, 2013

(54) METHODS FOR THE DIRECT CONVERSION OF CARBON DIOXIDE INTO A HYDROCARBON USING A METABOLICALLY ENGINEERED PHOTOSYNTHETIC MICROORGANISM

(75) Inventor: Stephen Anderson, Princeton, NJ (US)

(73) Assignee: Zuvachem, Inc., Lutherville, MD (US)

( * ) Notice: Subject to any disclaimer, the term of this patent is extended or adjusted under 35 U.S.C. 154(b) by 253 days.

(21) Appl. No.: 12/598,506

(22) PCT Filed: May 1, 2008

(86) PCT No.: PCT/US2008/005707
§ 371 (c)(1),
(2), (4) Date: Apr. 13, 2010

(87) PCT Pub. No.: WO2008/137092
PCT Pub. Date: Nov. 13, 2008

(65) Prior Publication Data
US 2010/0196982 A1    Aug. 5, 2010

Related U.S. Application Data

(60) Provisional application No. 60/927,102, filed on May 1, 2007.

(51) Int. Cl.
*C12N 9/88* (2006.01)

(52) U.S. Cl.
USPC ........................................ 435/167; 435/252.3

(58) Field of Classification Search
None
See application file for complete search history.

(56) References Cited

U.S. PATENT DOCUMENTS

| | | | |
|---|---|---|---|
| 4,698,304 A | 10/1987 | Fukuda et al. | |
| 5,578,472 A | 11/1996 | Ueda et al. | |
| 5,849,970 A | 12/1998 | Fall et al. | |
| 6,083,740 A | 7/2000 | Kodo et al. | |
| 6,812,000 B2 | 11/2004 | Wilkins et al. | |
| 7,129,392 B2 | 10/2006 | Hahn et al. | |
| 7,172,886 B2 | 2/2007 | Keasling et al. | |
| 8,048,658 B2 | 11/2011 | Clark et al. | |
| 2002/0072109 A1 | 6/2002 | Bayless et al. | |
| 2003/0175374 A1 | 9/2003 | Purcell | |
| 2005/0221467 A1 | 10/2005 | Brzostowicz et al. | |
| 2005/0239182 A1 | 10/2005 | Berzin | |
| 2006/0263863 A1 | 11/2006 | Hahn et al. | |
| 2007/0077616 A1 | 4/2007 | Keasling et al. | |
| 2007/0166782 A1 | 7/2007 | Keasling et al. | |
| 2007/0231861 A1 | 10/2007 | Millis et al. | |
| 2007/0254354 A1 | 11/2007 | Millis et al. | |
| 2007/0264708 A1 | 11/2007 | Bayless et al. | |
| 2008/0009055 A1 | 1/2008 | Lewnard | |
| 2008/0038805 A1* | 2/2008 | Melis ............................ 435/167 |
| 2008/0092829 A1 | 4/2008 | Renninger et al. | |
| 2008/0118964 A1 | 5/2008 | Huntley et al. | |
| 2008/0153080 A1 | 6/2008 | Woods et al. | |
| 2008/0155890 A1 | 7/2008 | Oyler | |
| 2008/0178354 A1 | 7/2008 | Chappell et al. | |
| 2008/0178739 A1 | 7/2008 | Lewnard et al. | |
| 2009/0028775 A1 | 1/2009 | O'Rear | |
| 2009/0029446 A1 | 1/2009 | O'Rear | |
| 2009/0087890 A1 | 4/2009 | Pyle et al. | |
| 2009/0126260 A1 | 5/2009 | Aravanis et al. | |
| 2009/0142816 A1 | 6/2009 | Strobel | |
| 2009/0148918 A1 | 6/2009 | Trimbur et al. | |
| 2009/0191599 A1 | 7/2009 | Devroe et al. | |
| 2009/0203070 A1 | 8/2009 | Devroe et al. | |
| 2009/0203102 A1 | 8/2009 | Cervin et al. | |
| 2009/0203115 A1 | 8/2009 | Busch et al. | |

FOREIGN PATENT DOCUMENTS

| | | |
|---|---|---|
| DE | 196 29 568 C1 | 1/1998 |
| WO | WO 84/00381 | 2/1984 |
| WO | WO 01/42455 A1 | 6/2001 |
| WO | WO 02/086094 | 10/2002 |
| WO | WO 2006/119052 A2 | 11/2006 |
| WO | WO 2007/011343 A1 | 1/2007 |
| WO | WO 2007/047805 A2 | 4/2007 |
| WO | WO 2007/070452 A1 | 6/2007 |
| WO | WO 2007/084477 A1 | 7/2007 |
| WO | WO 2007/098150 A2 | 8/2007 |
| WO | WO 2007/139924 A2 | 12/2007 |
| WO | WO 2007/139924 A3 | 12/2007 |
| WO | WO 2007/139925 A2 | 12/2007 |
| WO | WO 2008/003078 | 1/2008 |
| WO | WO 2008/130437 A2 | 10/2008 |
| WO | WO 2008/130437 A3 | 10/2008 |
| WO | WO 2008/151376 A1 | 12/2008 |
| WO | WO 2009/000019 A1 | 12/2008 |
| WO | WO 2009/036067 A3 | 3/2009 |
| WO | WO 2009/078712 A2 | 6/2009 |

(Continued)

OTHER PUBLICATIONS

Steve Davidson ECOS Magazine. Oct.-Dec. 2003; 117: 10-12.*
Witkowski et al. Biochemistry. Sep. 7, 1999; 38(36): 11643-50.*
Bonsang, B., et al., "Evidence for Marine Production of Isoprene," Geophysical Research Letters, Jun. 2, 1992, vol. 19, No. 11, pp. 1129-1132.
Daugulis, Andrew J., "Two-phase partitioning bioreactors: a new technology platform for destroying xenobiotics," TRENDS in Biotechnology, Nov. 2001, vol. 19, No. 11 pp. 457-462.
Deneris, E.S., et al., "Acid-catalyzed Formation of Isoprene from a Mevalonate-derived Product Using a Rat Liver Cytosolic Fraction," The Journal of Biological Chemistry, Feb. 10, 1985, vol. 260, No. 3, pp. 1382-1385.

(Continued)

*Primary Examiner* — Tekchand Saidha
*Assistant Examiner* — MD. Younus Meah
(74) *Attorney, Agent, or Firm* — Morgan Lewis & Bockius LLP; Jeffry S. Mann; Ada O. Wong

(57) ABSTRACT

The present invention relates to methods for the production of isoprene by the direct conversion of atmospheric carbon dioxide using metabolically engineered genetically engineered photosynthetic microorganisms. The present invention also relates to genetically engineered photosynthetic microorganisms, such as cyanobacteria, that are capable of producing isoprene from $CO_2$.

18 Claims, 18 Drawing Sheets

(56) References Cited

FOREIGN PATENT DOCUMENTS

| WO | WO 2009/087625 A1 | 7/2009 |
| WO | WO 2009/100231 A3 | 8/2009 |
| WO | WO 2009/111513 A1 | 9/2009 |
| WO | WO 2009/126843 A2 | 10/2009 |

OTHER PUBLICATIONS

Janikowski, T.B., et al., "Use of a two-phase partitioning bioreactor for degrading polycyclic aromatic hydrocarbons by a *Sphingomonas* sp.," Appl. Microbiol. Biotechnol. (2002) 59:368-376, DOI 10.1007/s00253-002-1011-y.

Moore, R.M., et al., "Production of isoprene by marine phytoplankton cultures," Geophysical Research Letters, Nov. 15, 1994, vol. 21, No. 23, pp. 2507-2510.

Newman, J., et al., "High-Level Production of Amorpha-4, 11-Diene in a Two-Phase Partitioning Bioreactor of Metabolically engineered *Escherichia coli*," Wiley InterScience, Jul. 28, 2006; www.interscience:wiley.com; DOI:10.1002/bit.21017.

Sherman, M, et al., "Isolation and Characterization of Isoprene Mutants of *Escherichia coli*," Journal of Bacteriology, Jul. 1989, pp. 3619-3628.

Tokarczyk, R., et al., "Production of volatile organohalogens by phytoplankton cultures," Geophysical Research Letters, Feb. 15, 1994, vol. 21, No. 4, pp. 285-288.

Davidson, S., "Light Factories" [Online] 2003 XP002501682, retrieved from the Internet: URL:http://www.publish.csiro.au/?act=view_file&file_id=EC117p10.pdf> [retrieved on Oct. 27, 2008].

Desplancq, D., et al., "Combining inducible protein overexpression with NMR-grade triple isotope labeling in the cyanobacterium *Anabaena* sp. PCC 7210" BioTechniques, 2005, vol. 39, No. 3, pp. 405-411.

Ershov, Y., et al., "Isopentenyl diphosphate isomerase deficiency in *Synechocystit* sp. strain PCC6803" XP004337163 ISSN:0014-5793, FEBS Letters, May 19, 2000, vol. 473, No. 3, pp. 337-340.

Iwai, M., et al., "Improved genetic transformation of the Thermophilic Cynabacterium, *Therrnosynechococcus elongatus* BP-1" XP002501684 ISSN: 0032-0781, Plant Cell Physiol., Feb. 2004, vol. 45, No. 2, pp. 171-175.

Miller, B., "Erstmalige Isolicrung cines Isoprensynthase-Gens und heterologe Expression des aus der Pappel stammenden Gens sowie Charakterisierung der Eingangsgene des Mevalonat-unabhängigen Isoprenoidbiosyntheseweges aus dem Cyanobakterium *Synethococcus ieopoliensis*" [Online] 2001, XP002501683, retrieved from the Internet: URL:http://kups.ub.uni-koeln.de/volltexte/2003/883/pdf/millerbarbara.pdf> [retrieved on Oct. 28, 2008].

Miller, B., et al., "First isolation of an isoprene synthase gene from poplar and successful expression of the gene in *Escherichia coli*" XP009107808, Planta, Jul. 1, 2001, vol. 213, No. 3, pp. 483-487.

Shaw, S., et al. Isoprene production by *Prochlorococcus*, a marine cyanobacterium, and other phytoplankton, Marine Chemistry, 2003, vol. 80, pp. 227-245.

International Preliminary Report on Patentability for International Application No. PCT/US2008/005707, issued Nov. 3, 2009.

International Search Report for International Application No. PCT/US2008/005707, mailed Nov. 14, 2008.

* cited by examiner

| Chemical name | 2-Methyl-1,3-butadiene |
| Other names | Isoprene |
| Chemical formula | $C_5H_8$ |
| Molecular mass | 68.11 g/mol |
| CAS number | [78-79-5] |
| Density | 0.681 g/cm$^3$ |
| Melting point | -145.95 °C |
| Boiling point | 34.067 °C |
| SMILES | C=C(C)C+C | isoprene

Isoprene Synthase (gi 13539551/emb CAC35696?):

```
  1 matellclhr plslthklfr nplpkviqat pltlklrcsv stenvsftet etesrrsany
 61 epnswdydfl lssdtdesie vykdkakkle aevrreinne kaefltllel ldnvqrlglg
121 yrfesdlrra ldrfvsaggf dgvtktslha talsfrllrq hgfevsqeaf sgfkdqngnf
181 lenlkedtka ilsiyeasfl alegenllde arvfsishlk elseskigke laeqvnhale
241 lplhrrtqrl earwsleayr kkedanqvll elslldynmi qsvyqrdlre tsrwwrrvgl
301 atklhfakdr llesfywavg vafepqysdc rnsvekmfsf vtllddiydv ygtldelelf
361 tdaverwdvn aindlpdymk lcflalynti nelaydnlkd kgenllpylt kawadlcnsf
421 lqeakwlynk stptfddyfg nawkssegpl qlifayfavv qnlkkeeien lqkyhdiisr
481 pshifrlcnd lasasaeiar qetansvscy mrtkgiseel atesvmnlid etckwmnkek
541 lggslfakpf vetalnlarq shctyhagda htspdeltrk rvlsvitepl lpfer
```

ORIGIN:

```
   1 cgcggccgcg tcgacgagag agagaaaatc ctgctgcagt tccattact agaggcatgg
  61 casctgaatt attgtgcttg cacgtcccha tctcacttac acacaaactg ttcagaaatc
 121 ccttacctaa agtcatccag gccactccct tasctttgaa actcagatgt tctgtaagca
 181 cagaaaacgt cagcttcacg gaaacagaaa cagaagccag acggtctgcc aattatgaac
 241 caaatagctg ggattatgat ttttgctgt ctcagacac tgacgaatcg attgaagtat
 301 acaaagacaa ggccaaaaag ctggaggctg aggtgagaag agagattaac aatgaaaagg
 361 cagagttttt gactctgctt gaactgatag ataatgtcca aaggttagga ttgggttacc
 421 ggttcgagtga tgacatagga agagccctcg acagattagt ttcttcaagga ggatttgatg
 481 gtgttacaaa aactagccct catgctactg ctcttagctt caggcttctc agacagcatg
 541 gctttgaggt ctctcaagaa gcgttcagtg gattcaagga tcaaaatggc aatttcttgg
 601 aaaaccttaa ggaggacacc aaggcaatac taagcctata tgaagcttca tttcttgcat
 661 tagaaggaga aaatatcctg gatgaggcca gggtgtttgc aatatccat ctcaaagagc
 721 tcagcgaaga aaagattgaa aagagctgg ccgaacaggt gaatcatgca ttggagcttc
 781 cattgcatcg cagacgcaa agactgaag ctgtttggag tattgaagca taccgtaaaa
 841 aggaagatgc aaatcaagta ctgctagaac ttgctatatt ggactacaac atgattcaat
 901 cagtatacca aagagatctt cgcgagacat caggtggtg gaggcgagtg ggtcttgcaa
 961 caaagttgca ttttgctaaa gacaggttaa ttgaagctt ttactgggca gttggagttg
1021 cgttcgaacc tcaatacagt gattgccgta attcagtagc aaaaatgttt tcatttgtaa
1081 caatcattga tgatatctat gatgtttatg gtactctgga tgagctggag ctatttcag
1141 atgctgtga gagatgggat gttaacgcca tcaatgatct tccggattat atgaagctct
1201 gcttcctagc tctctacaac actatcaatg agtagctta tgacaatctg aaggacaagg
1261 gggaaaacat tcttccatac ctaacaaaag agtgggcaga tttatgcast gcattcctac
1321 aagaagcaaa atggctgtac aataagtcca caccaacatt tgatgactat tcggaaatg
1381 catggaaatc atcctcaggg ctctttcac taattttgc ctactttgcc gtggttcaaa
1441 acatcaagaa agaggaaatt gaaaacttac aaaagtatca tgatatcatc agtaggcctt
1501 ccashcatctt tcgtcttgc aacgacctgg cttcagcatc ggctgagata gcgagaggtg
1561 aaactgcaaa ttccgtatcc tgtacgatga gtacaaaagg cattcctgag gaacttgcta
1621 ctgaatccgt aatgaattg atcgacgaaa cctgtaaaa gatgaacaaa gaaaagttg
1681 gtggctcttt gtttgcaaaa cctttgtcg aaacagctat taacttgca cggcaatccc
1741 attgcactta tcataacgga gatgcgcata cttcaccaga cgagctaact aggaaacgtg
1801 tcctgtcagt aatcacagag cctattctac ccttgagag ataaagtaa caggtttcc
1861 atgttgtcgt ctgcaagaac aaataacata tgctgcgtag aaaattaagc catgtaaata
1921 ggcttacct ccatgtccg cggagttttt gcagcagcaa gtacccrct gtattgtgga
1981 tggagagtat tgtatatttt cattcagatt acaggaaga ttatatatcc atttccttat
2041 tttgagtgca aaaaaaaaa aa
```

TRANSLATION:

```
3:                                                                   M   A   [SEQ ID NO: 5]
      CGCGGCCGCGTCGACGAGAGAGAGAAAATCCTGCTGCAGTTCCATTACTAGAGGCATGG       [SEQ ID NO: 4]
   1 ----------|----------|----------|----------|----------|----------| 60
      GCGCCGGCGCAGCTGCTCTCTCTCTTTTAGGACGACGTCAAGGTAATGATCTCCCTACC       [SEQ ID NO: 6]
```

FIGURE 3A

```
3:     T  E  L  L  C  L  H  R  P  I  S  L  T  H  K  L  F  R  N  P
       CAACTGAATTATTGTGCTTGCACCGTCCAATCTCACTGACACACAAACTGTTCAGAAATC
61     ---------!---------!---------!---------!---------!---------!  120
       GTTGACTTAATAACACGAACGTGGCAGGTTAGAGTGACTGTGTGTTTGACAAGTCTTTAG

3:     L  P  K  V  I  Q  A  T  P  L  T  L  K  L  R  C  S  V  S  T
       CCTTACCTAAAGTCATCCAGGCCACTCCCTTAACTTTGAAACTCAGATGTTCTGTAAGCA
121    ---------!---------!---------!---------!---------!---------!  180
       GGAATGGATTTCAGTAGGTCCGGTGAGGGAATTGAAACTTTGAGTCTACAAGACATTCGT

3:     E  N  V  S  F  T  E  T  E  T  E  A  R  R  S  A  N  Y  E  P
       CAGAAAACGTCAGCTTCACAGAAACAGAAACAGAAGCCAGACGGTCTGCCAATTATGAAC
181    ---------!---------!---------!---------!---------!---------!  240
       GTCTTTTGCAGTCGAAGTGTCTTTGTCTTTGTCTTCGGTCTGCCAGACGGTTAATACTTG

3:     N  S  W  D  Y  D  F  L  L  S  S  D  T  D  E  S  I  E  V  Y
       CAAATAGCTGGGATTATGATTTTTTGCTGTCTTCAGACACTGACGAATCGATTGAAGTAT
241    ---------!---------!---------!---------!---------!---------!  300
       GTTTATCGACCCTAATACTAAAAAACGACAGAAGTCTGTGACTGCTTAGCTAACTTCATA

3:     K  D  K  A  K  K  L  E  A  E  V  R  R  E  I  N  N  E  K  A
       ACAAAGACAAGGCCAAAAAGCTGGAGGCTGAGGTGAGAAGAGAGATTAACAATGAAAAGG
301    ---------!---------!---------!---------!---------!---------!  360
       TGTTTCTGTTCCGGTTTTTCGACCTCCGACTCCACTCTTCTCTCTAATTGTTACTTTTCC

3:     E  F  L  T  L  L  E  L  I  D  N  V  Q  R  L  G  L  G  Y  R
       CAGAGTTTTTGACTCTGCTTGAACTGATAGATAATGTCCAAAGGTTAGGATTGGGTTACC
361    ---------!---------!---------!---------!---------!---------!  420
       GTCTCAAAAACTGAGACGAACTTGACTATCTATTACAGGTTTCCAATCCTAACCCAATGG

3:     F  E  S  D  I  R  R  A  L  D  R  F  V  S  S  G  G  F  D  G
       GGTTCGAGAGTGACATAAGGAGAGCCCTCGACAGATTTGTTTCTTCAGGAGGATTTGATG
421    ---------!---------!---------!---------!---------!---------!  480
       CCAAGCTCTCACTGTATTCCTCTCGGGAGCTGTCTAAACAAAGAAGTCCTCCTAAACTAC

3:     V  T  K  T  S  L  H  A  T  A  L  S  F  R  L  L  R  Q  H  G
       GTGTTACAAAAACTAGCCTTCATGCTACTGCTCTTAGCTTCAGGCTTCTCAGACAGCATG
481    ---------!---------!---------!---------!---------!---------!  540
       CACAATGTTTTTGATCGGAAGTACGATGACGAGAATCGAAGTCCGAAGAGTCTGTCGTAC

3:     F  E  V  S  Q  E  A  F  S  G  F  K  D  Q  N  G  N  F  L  E
       GCTTTGAGGTCTCTCAAGAAGCGTTCAGTGGATTCAAGGATCAAAATGGCAATTTCTTGG
541    ---------!---------!---------!---------!---------!---------!  600
       CGAAACTCCAGAGAGTTCTTCGCAAGTCACCTAAGTTCCTAGTTTTACCGTTAAAGAACC

3:     N  L  K  E  D  T  K  A  I  L  S  L  Y  E  A  S  F  L  A  L
       AAAACCTTAAGGAGGACACCAAGGCAATACTAAGCCTATATGAAGCTTCATTTCTTGCAT
601    ---------!---------!---------!---------!---------!---------!  660
```

FIGURE 3B

```
                      TTTTGGAATTCCTCCTGTGGTTCCGTTATGATTCGGATATACTTCGAAGTAAAGAACGTA

3:       E   G   E   N   I   L   D   E   A   R   V   F   A   I   S   H   L   K   E   L
             TAGAAGGAGAAAATATCTTGGATGAGGCCAGGGTGTTTGCAATATCACATCTAAAAGAGC
 661     ---------!---------!---------!---------!---------!---------!  720
             ATCTTCCTCTTTTATAGAACCTACTCCGGTCCCACAAACGTTATAGTGTAGATTTTCTCG

3:       S   E   E   K   I   G   K   E   L   A   E   Q   V   N   H   A   L   E   L   P
             TCAGCGAAGAAAAGATTGGAAAAGAGCTGGCCGAACAGGTGAATCATGCATTGGAGCTTC
 721     ---------!---------!---------!---------!---------!---------!  780
             AGTCGCTTCTTTTCTAACCTTTTCTCGACCGGCTTGTCCACTTAGTACGTAACCTCGAAG

3:       L   H   R   R   T   Q   R   L   E   A   V   W   S   I   E   A   Y   R   K   K
             CATTGCATCGCAGGACGCAAAGACTAGAAGCTGTTTGGAGTATTGAAGCATACCGTAAAA
 781     ---------!---------!---------!---------!---------!---------!  840
             GTAACGTAGCGTCCTGCGTTTCTGATCTTCGACAAACCTCATAACTTCGTATGGCATTTT

3:       E   D   A   N   Q   V   L   L   E   L   A   I   L   D   Y   N   M   I   Q   S
             AGGAAGATGCAAATCAAGTACTGCTAGAACTTGCTATATTGGACTACAACATGATTCAAT
 841     ---------!---------!---------!---------!---------!---------!  900
             TCCTTCTACGTTTAGTTCATGACGATCTTGAACGATATAACCTGATGTTGTACTAAGTTA

3:       V   Y   Q   R   D   L   R   E   T   S   R   W   W   R   R   V   G   L   A   T
             CAGTATACCAAAGAGATCTTCGCGAGACATCAAGGTGGTGGAGGCGAGTGGGTCTTGCAA
 901     ---------!---------!---------!---------!---------!---------!  960
             GTCATATGGTTTCTCTAGAAGCGCTCTGTAGTTCCACCACCTCCGCTCACCCAGAACGTT

3:       K   L   H   F   A   K   D   R   L   I   E   S   F   Y   W   A   V   G   V   A
             CAAAGTTGCATTTTGCTAAAGACAGGTTAATTGAAAGCTTTTACTGGGCAGTTGGAGTTG
 961     ---------!---------!---------!---------!---------!---------!  1020
             GTTTCAACGTAAAACGATTTCTGTCCAATTAACTTTCGAAAATGACCCGTCAACCTCAAC

3:       F   E   P   Q   Y   S   D   C   R   N   S   V   A   K   M   F   S   F   V   T
             CGTTCGAACCTCAATACAGTGATTGCCGTAATTCAGTAGCAAAAATGTTTTCATTTGTAA
1021     ---------!---------!---------!---------!---------!---------!  1080
             GCAAGCTTGGAGTTATGTCACTAACGGCATTAAGTCATCGTTTTTACAAAAGTAAACATT

3:       I   I   D   D   I   Y   D   V   Y   G   T   L   D   E   L   E   L   F   T   D
             CAATCATTGATGATATCTATGATGTTTATGGTACTCTGGATGAGCTGGAGCTATTTACAG
1081     ---------!---------!---------!---------!---------!---------!  1140
             GTTAGTAACTACTATAGATACTACAAATACCATGAGACCTACTCGACCTCGATAAATGTC

3:       A   V   E   R   W   D   V   N   A   I   N   D   L   P   D   Y   M   K   L   C
             ATGCTGTTGAGAGATGGGATGTTAACGCCATCAATGATCTTCCGGATTATATGAAGCTCT
1141     ---------!---------!---------!---------!---------!---------!  1200
             TACGACAACTCTCTACCCTACAATTGCGGTAGTTACTAGAAGGCCTAATATACTTCGAGA
```

FIGURE 3C

```
     3:     F   L   A   L   Y   N   T   I   N   E   I   A   Y   D   N   L   K   D   K   G
            GCTTCCTAGCTCTCTACAACACTATCAATGAGATAGCTTATGACAATCTGAAGGACAAGG
     1201   ---------!---------!---------!---------!---------!---------!  1260
            CGAAGGATCGAGAGATGTTGTGATAGTTACTCTATCGAATACTGTTAGACTTCCTGTTCC

3:     E   N   I   L   P   Y   L   T   K   A   W   A   D   L   C   N   A   F   L   Q
            GGGAAAACATTCTTCCATACCTAACAAAAGCGTGGGCAGATTTATGCAATGCATTCCTAC
     1261   ---------!---------!---------!---------!---------!---------!  1320
            CCCTTTTGTAAGAAGGTATGGATTGTTTTCGCACCCGTCTAAATACGTTACGTAAGGATG

3:     E   A   K   W   L   Y   N   K   S   T   P   T   F   D   D   Y   F   G   N   A
            AAGAAGCAAAATGGCTGTACAATAAGTCCACACCAACATTTGATGACTATTTCGGAAATG
     1321   ---------!---------!---------!---------!---------!---------!  1380
            TTCTTCGTTTTACCGACATGTTATTCAGGTGTGGTTGTAAACTACTGATAAAGCCTTTAC

3:     W   K   S   S   S   G   P   L   Q   L   I   F   A   Y   F   A   V   V   Q   N
            CATGGAAATCATCCTCAGGGCCTCTTCAACTAATTTTTGCCTACTTTGCCGTGGTTCAAA
     1381   ---------!---------!---------!---------!---------!---------!  1440
            GTACCTTTAGTAGGAGTCCCGGAGAAGTTGATTAAAAACGGATGAAACGGCACCAAGTTT

3:     I   K   K   E   E   I   E   N   L   Q   K   Y   H   D   I   I   S   R   P   S
            ACATCAAGAAAGAGGAAATTGAAAACTTACAAAAGTATCATGATATCATCAGTAGGCCTT
     1441   ---------!---------!---------!---------!---------!---------!  1500
            TGTAGTTCTTTCTCCTTTAACTTTTGAATGTTTTCATAGTACTATAGTAGTCATCCGGAA

3:     H   I   F   R   L   C   N   D   L   A   S   A   S   A   E   I   A   R   G   E
            CCCACATCTTTCGTCTTTGCAACGACCTGGCTTCAGCATCGGCTGAGATAGCGAGAGGTG
     1501   ---------!---------!---------!---------!---------!---------!  1560
            GGGTGTAGAAAGCAGAAACGTTGCTGGACCGAAGTCGTAGCCGACTCTATCGCTCTCCAC

3:     T   A   N   S   V   S   C   Y   M   R   T   K   G   I   S   E   E   L   A   T
            AAACTGCGAATTCCGTATCCTGCTACATGCGTACAAAAGGCATTTCTGAGGAACTTGCTA
     1561   ---------!---------!---------!---------!---------!---------!  1620
            TTTGACGCTTAAGGCATAGGACGATGTACGCATGTTTTCCGTAAAGACTCCTTGAACGAT

3:     E   S   V   M   N   L   I   D   E   T   C   K   K   M   N   K   E   K   L   G
            CTGAATCCGTAATGAATTTGATCGACGAAACCTGTAAAAAGATGAACAAAGAAAAGCTTG
     1621   ---------!---------!---------!---------!---------!---------!  1680
            GACTTAGGCATTACTTAAACTAGCTGCTTTGGACATTTTTCTACTTGTTTCTTTTCGAAC

3:     G   S   L   F   A   K   P   F   V   E   T   A   I   N   L   A   R   Q   S   H
            GTGGCTCTTTGTTTGCAAAACCTTTTGTCGAAACAGCTATTAACCTTGCACGGCAATCCC
     1681   ---------!---------!---------!---------!---------!---------!  1740
            CACCGAGAAACAAACGTTTTGGAAAACAGCTTTGTCGATAATTGGAACGTGCCGTTAGGG

3:     C   T   Y   H   N   G   D   A   H   T   S   P   D   E   L   T   R   K   R   V
            ATTGCACTTATCATAACGGAGATGCGCATACTTCACCAGACGAGCTAACTAGGAAACGTG
     1741   ---------!---------!---------!---------!---------!---------!  1800
```

FIGURE 3D

```
                TAACGTGAATAGTATTGCCTCTACGCGTATGAAGTGGTCTGCTCGATTGATCCTTTGCAC

3:     L    S    V    I    T    E    P    I    L    P    F    E    R    *
           TCCTGTCAGTAATCACAGAGCCTATTCTACCCTTTGAGAGATAAAAGTAACAGGTTTTCC
1801       ------------|------------|------------|------------|------------| 1860
           AGGACAGTCATTAGTGTCTCGGATAAGATGGGAAACTCTCTATTTTCATTGTCCAAAAGG

ATGTTGTCGTCTGCAAGAACAAATAACATATGCTGCGTAGAAAATTAAGCCATGTAAATA
1861       ------------|------------|------------|------------|------------| 1920
           TACAACAGCAGACGTTCTTGTTTATTGTATACGACGCATCTTTTAATTCGGTACATTTAT

GGCTTTAACTCCATGTCCGGCGGAGTTTTTGCAGCAGCAAGTACCCTCCTGTATTGTGGA
1921       ------------|------------|------------|------------|------------| 1980
           CCGAAATTGAGGTACAGGCCGCCTCAAAAACGTCGTCGTTCATGGGAGGACATAACACCT

TGGAGAGTATTGTATATTTTCATTCAGATTACAAGGAAGATTATATATCCATTTTCTTAT
1981       ------------|------------|------------|------------|------------| 2040
           ACCTCTCATAACATATAAAAGTAAGTCTAATGTTCCTTCTAATATATAGGTAAAAGAATA

TTTGAGTGCAAAAAAAAAAAAAA        [SEQ ID NO: 4 cont.]
2041       ------------|------------|-- 2062
           AAACTCACGTTTTTTTTTTTTTT         [SEQ ID NO: 6 cont.]
```

FIGURE 3E

Alignments of four isoprene synthase sequences from genus Populus

```
UNIPARC_UPI00000A93DA    MATELLCLHRPISLTHKLFRNPLPKVIQATPLTLKLRCSVSTENVSFTET  50   [SEQ ID NO: 7]
AAQ16588                 MATELLCLHRPISLTHKLFRNPLPKVIQATPLTLKLRCSVSTENVSFSET  50   [SEQ ID NO:8]
BAD98243                 MATELLCLHRPISLTHKLFRNPLPKVIQATPLTLKLRCSVSTENVSFTET  50   [SEQ ID NO:9]
CAL69918                 MATELLCLHRPISLTHKLFRNPLPKVIQATPLTLKLRCSVSTENVSFTET  50
                         ********************************************** ***        [SEQ ID NO:10]

UNIPARC_UPI00000A93DA    ETEARRSANYEPNSWDYDFLLSSDTDESIEVYKDKAKKLEAEVRREINNE  100
AAQ16588                 ETETRRSANYEPNSWDYDYLLSSDTDESIEVHKDKAKKLEAEVRREINNE  100
BAD98243                 ETEARRSANYEPNSWDYDYLLSSDTDESIEVYKDKAKKLEAEVRREINNE  100
CAL69918                 ETETRRSANYEPNSWDYDYLLSSDTDESIEVYKDKAKKLEAEVRREINNE  100
                         *** ************* *************:*****************

UNIPARC_UPI00000A93DA    KAEFLTLLELIDNVQRLGLGYRFESDIRRALDRFVSSGGFDGVTKTSLHA  150
AAQ16588                 KAEFLTLLELIDNVQRLGLGYRFESDIRRALDRFVSSGGFDGVTKTSLHG  150
BAD98243                 KAEFLTLLELIDNVQRLGLGYRFESDIRCALDRFVSSGGFDAVTKTSLHG  150
CAL69918                 KAEFLTLPELIDNVQRLGLGYRFESDIRRALDRFVSSGGFDAVTKTSLHA  150
                         ******* ******************* ************.******.

UNIPARC_UPI00000A93DA    TALSFRLLRQHGFEVSQEAFSGFKDQNGNFLENLKEDTKAILSLYEASFL  200
AAQ16588                 TALSFRLLRQHGFEVSQEAFSGFKDQNGNFLENLKEDTKAILSLYEASFL  200
BAD98243                 TALSFRLLRQHGFEVSQEAFSGFKDQNGNFLENLKEDIKAILSLYEASFL  200
CAL69918                 TALSFRLLRQHGFEVSQEAFSGFKDQNGNFLKNLKEDIKAILSLYEASFL  200
                         ******************************* :**** **********

UNIPARC_UPI00000A93DA    ALEGENILDEARVFAISHLKELSEEKIGKELAEQVNHALELPLHRRTQRL  250
AAQ16588                 ALEGENILDEAKVFAISHLKELSEEKIGKELAEQVSHALELPLHRRTQRL  250
BAD98243                 ALEGENILDEAKVFAISHLKELSEEKIGKELAEQVNHALELPLHRRTQRL  250
CAL69918                 ALEGENILDEAKVFAISHLKELSEEKICKDLAEQVNHALELPLHRRTQRL  250
                         *********** ************** *:.***** ************

UNIPARC_UPI00000A93DA    EAVWSIEAYRKKEDANQVLLELAILDYNMIQSVYQRDLRETSRWWRRVGL  300
AAQ16588                 EAVWSIEAYRKKEDANQVLLELAILDYNMIQSVYQRDLRETSRWWRRVGL  300
BAD98243                 EAVWSIEAYRKKEDANQVLLELAILDYNMIQSVYQRDLRETSRWWRRVGL  300
CAL69918                 EAVWSIEAYRKKEDADQVLLELAILDYNMIQSVYQRDLRETSRWWRRVGL  300
                         *************** *********************************

UNIPARC_UPI00000A93DA    ATKLHFAKDRLIESFYWAVGVAFEPQYSDCRNSVAKMFSFVTIIDDIYDV  350
AAQ16588                 ATKLHFARDRLIESFYWAVGVAFEPQYSDCRNSVAKMFSFVTIIDDIYDV  350
BAD98243                 ATKLHFARDRLIESFYWAVGVAFEPQYSDCRNSVAKMFSFVTIIDDIYDV  350
CAL69918                 ATKLHFARDRLIESFYWAVGVAFEPQYSDCRNSVAKMFSFVTIIDDIYDV  350
                         ******:******************************************

UNIPARC_UPI00000A93DA    YGTLDELELFTDAVERWDVNAINDLPDYMKLCFLALYNTINEIAYDNLKD  400
AAQ16588                 YGTLDELELFTDAVERWDVNAINDLPDYMKLCFLALYNTINEIAYDNLKD  400
BAD98243                 YGTLDELELFTDAVERWDVNAINDLPDYMKLCFLALYNTINEIAYDNLKD  400
CAL69918                 YGTLDELELFTDAVERWDVNAIDDLPDYMKLCFLALYNTINEIAYDNLKD  400
                         ********************** **************************

UNIPARC_UPI00000A93DA    KGENILPYLTKAWADLCNAFLQEAKWLYNKSTPTFDDYFGNAWKSSSGPL  450
AAQ16588                 KGENILPYLTKAWADLCNAFLQEAKWLYNKSTPTFDDYFGNAWKSSSGPL  450
BAD98243                 KGENILPYLTKAWADLCNAFLQEAKWLYNKSTPTFDDYFGNAWKSSSGPL  450
CAL69918                 KGENILPYLTKAWADLCNAFLQEAKWLYNKSTPTFDEYFGNAWKSSSGPL  450
                         ************************************:************

UNIPARC_UPI00000A93DA    QLIFAYFAVVQNIKKEEIENLQKYHDIISRPSHIFRLCNDLASASAEIAR  500
```

FIGURE 4A

```
AAQ16588                    QLIFAYFAVVQNIKKEEIENLQKYHDIISRPSHIFRLCNDLASASAEIAR  500
BAD98243                    QLVFAYFAVVQNIKKEEIENLQKYHDTISRPSHIFRLCNDLASASAEIAR  500
CAL69918                    QLVFAYFAVVQNIKKEEIDNLQKYHDIISRPSHIFRLCNDLASASAEIAR  500
                             * ****************:*******:***********************

UNIPARC_UPI00000A93DA       GETANSVSCYMRTKGISEELATESVMNLIDETCKKMNKEKLGGSLFAKPF  550
AAQ16588                    GETANSVSCYMRTKGISEELATESVMNLIDETWKKMNKEKLGGSLFAKPF  550
BAD98243                    GETANSVSCYMRTKGISEELATESVMNLIDETWKKMNKEKLGGSLFAKPF  550
CAL69918                    GETANSVSCYMRTKGISEELATESVMNLIDETWKKMNKEKLGGSLFAKPF  550
                            *******************************.*****************

UNIPARC_UPI00000A93DA       VETAINLARQSHCTYHNGDAHTSPDELTRKRVLSVITEPILPFER 595    [SEQ ID NO 7 cont.]
AAQ16588                    VETAINLARQSHCTYHNGDAHTSPDELTRKRVLSVITEPILPFER 595    [SEQ ID NO: 8 cont.]
BAD98243                    VETAINLARQSHCTYHNGDAHTSPDELTRKRVLSVITEPILPFER 595    [SEQ ID NO:9 cont.]
CAL69918                    VETAINLARQSHCTYHNGDAHTSPDELTRKRVLSVITEPILPFER 595    [SEQ ID NO:10 cont.]
                            ********************************************
```

*PLEASE NOTE: Showing colors on large alignments is slow.*

FIGURE 4B

MEP pathway in cyanobacteria to produce IPP and DMAPP

DXS- 1-deoxy-D-xylulose-5-phosphate synthase
DXR-1-deoxy-D-xylulose-5-phosphate reducto isomerase
MCT-MEP cytidyltransferase
CMK-4-(cytidine 5'phospho-)2C-methylerythritol kinase
MECPS- MECPsynthase
IPI-Isopentenyl pyrophosphate isomerase CTGCAGGAGCTGTTGACAATTAATCATCGAACTAGTTTAATGTGTGGAATTGTGAGCGGATAACAATTA
AGCTTAGGAGGAATTCTTATGGGTCATCACCATCACCATCACCATCACAGTGGTGCAACTGAATTATTG
TGCTTGCACCGTCCAATCTCACTGACACACAAACTGTTCCGAAATCCCTTACCTAAAGTCATCCAGGCC
ACTCCCTTAACTTTGAAACTCCGATGTTCTGTAAGCACAGAAAACGTCAGCTTCACAGAAACAGAAACA
GAAGCCCGACGGTCTGCCAATTATGAACCAAATAGCTGGGATTATGATTTTTTGCTGTCTTCAGACACT
GACGAATCGATTGAAGTATACAAAGACAAGGCCAAAAAGCTGGAGGCTGAGGTGCGACGAGAGATTAAC
AATGAAAAGGCAGAGTTTTTGACTCTGCTTGAACTGATTGATAATGTCCAAAGGTTAGGATTGGGTTAC
CGGTTCGAGAGTGACATTAGGCGAGCCCTCGACCGATTTGTTTCTTCAGGAGGATTTGATGGTGTTACA
AAAACTAGCCTTCATGCTACTGCTCTTAGCTTCAGGCTTCTCCGACAGCATGGCTTTGAGGTCTCTCAA
GAAGCGTTCAGTGGATTCAAGGATCAAAATGGCAATTTCTTGGAAAACCTTAAGGAGGACACCAAGGCA
ATTCTAAGCCTATATGAAGCCTCATTTCTTGCATTAGAAGGAGAAAATATCTTGGATGAGGCCAGGGTG
TTTGCAATTTCACATCTAAAAGAGCTCAGCGAAGAAAAGATTGGAAAAGAGCTGGCCGAACAGGTGAAT
CATGCATTGGAGCTTCCATTGCATCGCAGGACGCAACGACTAGAAGCTGTTTGGAGTATTGAAGCATAC
CGTAAAAAGGAAGATGCAAATCAAGTACTGCTAGAACTTGCTATTTTGGACTACAACATGATTCAATCA
GTATACCAACGTGATCTTCGTGAGACATCAAGGTGGTGGAGGCGAGTGGGTCTTGCAACAAAGTTGCAT
TTTGCTAAAGACAGGTTAATTGAGAGCTTTTACTGGGCAGTTGGAGTTGCGTTCGAACCTCAATACAGT
GATTGCCGTAATTCAGTAGCAAAAATGTTTTCATTTGTAACAATCATTGATGATATCTATGATGTTTAT
GGTACTCTGGATGAGCTGGAGCTATTTACAGATGCTGTTGAGCGATGGGATGTTAACGCCATCAATGAT
CTTCCGGATTATATGAAGCTCTGCTTCCTAGCTCTCTACAACACTATCAATGAGATTGCTTATGACAAT
CTGAAGGACAAGGGGGAAAACATTCTTCCATACCTAACAAAAGCGTGGGCAGATTTATGCAATGCATTC
CTACAAGAAGCAAAATGGCTGTACAATAAGTCCACACCAACATTTGATGACTATTTCGGAAATGCATGG
AAATCATCCTCAGGGCCTCTTCAACTAATTTTTGCCTACTTTGCCGTGGTTCAAAACATCAAGAAAGAG
GAAATTGAAACTTACAAAAGTATCATGATATCATCAGTAGGCCTTCCCACATCTTTCGTCTTTGCAAC
GACCTGGCTTCAGCATCGGCTGAGATTGCACGAGGTGAAACTGCCAATTCCGTATCCTGCTACATGCGT
ACAAAAGGCATTTCTGAGGAACTTGCTACTGAATCCGTAATGAATTTGATCGACGAAACCTGGAAAAAG
ATGAACAAAGAAAGCTCGGTGGCTCTTTGTTTGCAAAACCTTTTGTCGAAACAGCTATTAACCTTGCA
CGGCAATCCCATTGCACTTATCATAACGGAGATGCGCATACTTCACCAGACGAGCTAACTAGGAAACGT
GTCCTGTCAGTAATCACAGAGCCTATTCTACCCTTTGAGCGATAATAGGTACC

```
    CTGCAGGAGCTGTTGACAATTAATCATCGAACTAGTTTAATGTGTGGAATTGTGAGCGGA
1   ---------!---------!---------!---------!---------!---------!  60
```

Figure 6A. Synthetic isoprene synthase gene_v2.2

```
                                            M  G  H  H  H  H  H  H  H  S  [SEQ ID NO: 12]
        TAACAATTAAGCTTAGGAGGAATTCTTATGGGTCATCACCATCACCATCACCATACAGT  [SEQ ID NO: 11]
   61   ----+----|----+----|----+----|----+----|----+----|----+----|  120

G  A  T  E  L  L  C  L  H  R  P  I  S  L  T  R  K  L  F  R
        GGTGCAACTGAATTATTGTGCTTGCACCGTCCAATCTCACTGACACACAAACTGTTCCGA
  121   ----+----|----+----|----+----|----+----|----+----|----+----|  180

N  P  L  P  K  V  I  Q  A  T  P  L  T  L  K  L  R  C  S  V
        AATCCCTTACCTAAAGTCATCCAGGCCACTCCCTTAACTTTGAAACTCCGATGTTCTGTA
  181   ----+----|----+----|----+----|----+----|----+----|----+----|  240

S  T  E  N  V  S  F  T  E  T  E  T  E  A  R  R  S  A  N  Y
        AGCACAGAAAACGTCAGCTTCACAGAAACAGAAACAGAAGCCCGACGGTCTGCCAATTAT
  241   ----+----|----+----|----+----|----+----|----+----|----+----|  300

E  P  N  S  W  D  Y  D  F  L  L  S  S  D  T  D  E  S  I  E
        GAACCAAATAGCTGGGATTATGATTTTTTGCTGTCTTCAGACACTGACGAATCGATTGAA
  301   ----+----|----+----|----+----|----+----|----+----|----+----|  360

V  Y  K  D  K  A  K  K  L  E  A  E  V  R  R  E  I  N  N  E
        GTATACAAAGACAAGGCCAAAAAGCTGGAGGCTGAGGTGCGACGAGAGATTAACAATGAA
  361   ----+----|----+----|----+----|----+----|----+----|----+----|  420

K  A  E  F  L  T  L  L  E  L  I  D  N  V  Q  R  L  G  L  G
        AAGGCAGAGTTTTTGACTCTGCTTGAACTCATTGATAATGTCCAAAGGTTAGGATTGGGT
  421   ----+----|----+----|----+----|----+----|----+----|----+----|  480

Y  R  F  E  S  D  I  R  R  A  L  D  R  F  V  S  S  G  G  F
        TACCGGTTCGAGAGTGACATTAGGCGAGCCCTCGACCGATTTGTTTCTTCAGGAGGATTT
  481   ----+----|----+----|----+----|----+----|----+----|----+----|  540

D  G  V  T  K  T  S  L  H  A  T  A  L  S  F  R  L  L  R  Q
        GATGGTGTTACAAAAACTAGCCTTCATGCTACTGCTCTTAGCTTCAGGCTTCTCCGACAG
  541   ----+----|----+----|----+----|----+----|----+----|----+----|  600

H  G  F  E  V  S  Q  E  A  F  S  G  F  K  D  Q  N  G  N  F
        CATGGCTTTGAGGTCTCTCAAGAAGCGTTCAGTGGATTCAAGGATCAAAATGGCAATTTC
  601   ----+----|----+----|----+----|----+----|----+----|----+----|  660

L  E  N  L  K  E  D  T  K  A  I  L  S  L  Y  E  A  S  F  L
        TTGGAAAACCTTAAGGAGGACACCAAGGCAATTCTAAGCCTATATGAAGCCTCATTTCTT
  661   ----+----|----+----|----+----|----+----|----+----|----+----|  720

A  L  E  G  E  N  I  L  D  E  A  R  V  F  A  I  S  H  L  K
        GCATTAGAAGGAGAAAATATCTTGGATGAGGCCAGGGTGTTTGCAATTTCACATCTAAAA
  721   ----+----|----+----|----+----|----+----|----+----|----+----|  780

E  L  S  E  E  K  I  G  K  E  L  A  E  Q  V  N  H  A  L  E
        GAGCTCAGCGAAGAAAAGATTGGAAAAGAGCTGGCCGAACAGGTGAATCATGCATTGGAG
```

L  P  L  H  R  R  T  Q  R  L  E  A  V  W  S  I  E  A  Y  R
      CTTCCATTGCATCGCAGGACGCAACGACTAGAAGCTGTTTGGAGTATTGAAGCATACCGT
841 ---------!---------!---------!---------!---------!---------! 900

K  K  E  D  A  N  Q  V  L  L  E  L  A  I  L  D  Y  N  M  I
      AAAAAGGAAGATGCAAATCAAGTACTGCTAGAACTTGCTATTTTGGACTACAACATGATT
901 ---------!---------!---------!---------!---------!---------! 960

Q  S  V  Y  Q  R  D  L  R  E  T  S  R  W  W  R  R  V  G  L
      CAATCAGTATACCAACGTGATCTTCGTGAGACATCAAGGTGGTGGAGGCGAGTGGGTCTT
961 ---------!---------!---------!---------!---------!---------! 1020

A  T  K  L  H  F  A  K  D  R  L  I  E  S  F  Y  W  A  V  G
      GCAACAAAGTTGCATTTTGCTAAAGACAGGTTAATTGAGAGCTTTTACTGGGCAGTTGGA
1021 ---------!---------!---------!---------!---------!---------! 1080

V  A  F  E  P  Q  Y  S  D  C  R  N  S  V  A  K  M  F  S  F
      GTTGCGTTCGAACCTCAATACAGTGATTGCCGTAATTCAGTAGCAAAAATGTTTTCATTT
1081 ---------!---------!---------!---------!---------!---------! 1140

V  T  I  I  D  D  I  Y  D  V  Y  G  T  L  D  E  L  E  L  F
      GTAACAATCATTGATGATATCTATGATGTTTATGGTACTCTGGATGAGCTGGAGCTATTT
1141 ---------!---------!---------!---------!---------!---------! 1200

T  D  A  V  E  R  W  D  V  N  A  I  N  D  L  P  D  Y  M  K
      ACAGATGCTGTTGAGCGATGGGATGTTAACGCCATCAATGATCTTCCGGATTATATGAAG
1201 ---------!---------!---------!---------!---------!---------! 1260

L  C  F  L  A  L  Y  N  T  I  N  E  I  A  Y  D  N  L  K  D
      CTCTGCTTCCTAGCTCTCTACAACACTATCAATGAGATTGCTTATGACAATCTGAAGGAC
1261 ---------!---------!---------!---------!---------!---------! 1320

K  G  E  N  I  L  P  Y  L  T  K  A  W  A  D  L  C  N  A  F
      AAGGGGGAAAACATTCTTCCATACCTAACAAAAGCGTGGGCAGATTTATGCAATGCATTC
1321 ---------!---------!---------!---------!---------!---------! 1380

L  Q  E  A  K  W  L  Y  N  K  S  T  P  T  F  D  D  Y  F  G
      CTACAAGAAGCAAAATGGCTGTACAATAAGTCCACACCAACATTTGATGACTATTTCGGA
1381 ---------!---------!---------!---------!---------!---------! 1440

N  A  W  K  S  S  S  G  P  L  Q  L  I  F  A  Y  F  A  V  V
      AATGCATGGAAATCATCCTCAGGGCCTCTTCAACTAATTTTTGCCTACTTTGCCGTGGTT
1441 ---------!---------!---------!---------!---------!---------! 1500

Q  N  I  K  K  E  E  I  E  N  L  Q  K  Y  H  D  I  I  S  R
      CAAAACATCAAGAAGAGGAAATTGAAAACTTACAAAAGTATCATGATATCATCAGTAGG
1501 ---------!---------!---------!---------!---------!---------! 1560
```

FIGURE 6C

```
                P  S  H  I  F  R  L  C  N  D  L  A  S  A  S  A  E  I  A  R
         CCTTCCCACATCTTTCGTCTTTGCAACGACCTGGCTTCAGCATCGGCTGAGATTGCACGA
1561     ------------|----------|----------|----------|----------|----------| 1620

G  E  T  A  N  S  V  S  C  Y  M  R  T  K  G  I  S  E  E  L
         GGTGAAACTGCCAATTCCGTATCCTGCTACATGCGTACAAAAGGCATTTCTGAGGAACTT
1621     ------------|----------|----------|----------|----------|----------| 1680

A  T  E  S  V  M  N  L  I  D  E  T  N  K  K  M  N  K  E  K
         GCTACTGAATCCGTAATGAATTTGATCGACGAAACCTGGAAAAAGATGAACAAAGAAAAG
1681     ------------|----------|----------|----------|----------|----------| 1740

L  G  G  S  L  F  A  K  P  F  V  E  T  A  I  N  L  A  R  Q
         CTCGGTGGCTCTTTGTTTGCAAAACCTTTTGTCGAAACAGCTATTAACCTTGCACGGCAA
1741     ------------|----------|----------|----------|----------|----------| 1800

S  H  C  T  Y  H  N  G  D  A  H  T  S  P  D  E  L  T  R  K
         TCCCATTGCACTTATCATAACGGAGATGCGCATACTTCACCAGACGAGCTAACTAGGAAA
1801     ------------|----------|----------|----------|----------|----------| 1860

R  V  L  S  V  I  T  E  P  I  L  P  F  E  R  *             [SEQ ID NO: 12 cont.]
         CGTGTCCTGTCAGTAATCACAGAGCCTATTCTACCCTTTGAGCGATAATAGCTACC      [SEQ ID NO: 11 cont.]
1861     ------------|----------|----------|----------|----------|---------- 1916
```

FIGURE 6D

```
                TTTTGGAATTCCTCCTGTGGTTCCGTTATGATTCGGATATACTTCGAAGTAAAGAACGTA  [SEQ ID NO: 13]

3:     E  G  E  N  I  L  D  E  A  R  V  F  A  I  S  H  L  K  S  L    [SEQ ID NO: 14]
            TAGAAGGAGAAAATATCTTGGATGAGGCCAGGGTGTTTGCAATATCACATCTAAAAGAGC
    661     ------------|------------|------------|------------|------------|------------| 720
            ATCTTCCTCTTTTATAGAACCTACTCCGGTCCCACAAACGTTATAGTGTAGATTTTCTCG    [SEQ ID NO: 15]

3:     S  E  R  K  I  G  K  E  L  A  E  Q  V  N  H  A  L  E  L  P
            TCAGCGAAGAAAAGATTGGAAAAGAGCTGGCCGAACAGGTGAATCATGCATTGGAGCTTC
    721     ------------|------------|------------|------------|------------|------------| 780
            AGTCGCTTCTTTTCTAACCTTTTCTCGACCGGCTTGTCCACTTAGTACGTAACCTCGAAG

3:     L  H  R  R  T  Q  R  L  E  A  V  W  S  I  E  A  Y  R  K  K
            CATTGCATCGCAGGACGCAAAGACTAGAAGCTGTTTGGAGTATTGAAGCATACCGTAAAA
    781     ------------|------------|------------|------------|------------|------------| 840
            GTAACGTAGCGTCCTGCGTTTCTGATCTTCGACAAACCTCATAACTTCGTATGGCATTTT

3:     E  D  A  N  Q  V  L  L  E  L  A  I  L  D  Y  N  M  I  Q  S
            AGGAAGATGCAAATCAAGTACTGCTAGAACTTGCTATATTGGACTACAACATGATTCAAT
    841     ------------|------------|------------|------------|------------|------------| 900
            TCCTTCTACGTTTAGTTCATGACGATCTTGAACGATATAACCTGATGTTGTACTAAGTTA

3:     V  Y  Q  R  D  L  R  E  T  S  R  W  R  R  V  G  L  A  T
            CAGTATACCAAAGAGATCTTCGCGAGACATCAAGGTGGTGGAGGCGACTGGGTCTTGCAA
    901     ------------|------------|------------|------------|------------|------------| 960
            GTCATATGGTTTCTCTAGAAGCGCTCTGTAGTTCCACCACCTCCGCTGACCCAGAACGTT

3:     K  L  H  F  A  K  D  R  L  I  E  S  F  Y  W  A  V  G  V  A
            CAAAGTTGCATTTTGCTAAAGACAGGTTAATTGAAAGCTTTTACTGGGCAGTTGGAGTTG
    961     ------------|------------|------------|------------|------------|------------| 1020
            GTTTCAACGTAAAACGATTTCTGTCCAATTAACTTTCGAAAATGACCCGTCAACCTCAAC

3:     F  E  P  Q  Y  S  D  C  R  N  S  V  A  K  M  F  S  F  V  T
            CGTTCGAACCTCAATACAGTGATTGCCGTAATTCAGTAGCAAAAATGTTTTCATTTGTAA
    1021    ------------|------------|------------|------------|------------|------------| 1080
            GCAAGCTTGGAGTTATGTCACTAACGGCATTAAGTCATCGTTTTTACAAAAGTAAACATT

3:     I  I  D  D  I  T  D  V  Y  G  T  L  D  E  L  E  L  F  T  D
            CAATCATTGATGATATCTATGATGTTTATGGTACTCTGGATGAGCTGGAGCTATTTACAG
    1081    ------------|------------|------------|------------|------------|------------| 1140
            GTTAGTAACTACTATAGATACTACAAATACCATGAGACCTACTCGACCTCGATAAATGTC

3:     A  V  E  R  W  D  V  N  A  I  N  D  L  P  D  Y  M  K  L  C
            ATGCTGTTGAGAGATGGGATGTTAACGCCATCAATGATCTTCCGGATTATATGAAGCTCT
    1141    ------------|------------|------------|------------|------------|------------| 1200
            TACGACAACTCTCTACCCTACAATTGCGGTAGTTACTAGAAGGCCTAATATACTTCGAGA
```

FIGURE 6E

```
3:      F   L   A   L   Y   N   T   I   N   E   I   A   Y   D   N   L   K   D   K   G
        GCTTCCTAGCTCTCTACAACACTATCAATGAGATAGCTTATGACAATCTGAAGGACAAGG
1201    ---------!---------!---------!---------!---------!---------! 1260
        CGAAGGATCGAGAGATGTTGTGATAGTTACTCTATCGAATACTGTTAGACTTCCTGTTCC

3:      E   N   I   L   P   Y   L   T   K   A   W   A   D   L   C   N   A   F   L   Q
        GGGAAAACATTCTTCCATACCTAACAAAAGCGTGGGCAGATTTATGCAATGCATTCCTAC
1261    ---------!---------!---------!---------!---------!---------! 1320
        CCCTTTTGTAAGAAGGTATGGATTGTTTTCGCACCCGTCTAAATACGTTACGTAAGGATG

3:      E   A   K   W   L   Y   N   K   S   T   P   T   F   D   D   Y   F   G   N   A
        AAGAAGCAAAATGGCTGTACAATAAGTCCACACCAACATTTGATGACTATTTCGGAAATG
1321    ---------!---------!---------!---------!---------!---------! 1380
        TTCTTCGTTTTACCGACATGTTATTCAGGTGTGGTTGTAAACTACTGATAAAGCCTTTAC

3:      W   K   S   S   S   G   P   L   Q   L   I   F   A   Y   F   A   V   V   Q   N
        CATGGAAATCATCCTCAGGGCCTCTTCAACTAATTTTTGCCTACTTTGCCGTGGTTCAAA
1381    ---------!---------!---------!---------!---------!---------! 1440
        GTACCTTTAGTAGGAGTCCCGGAGAAGTTGATTAAAAACGGATGAAACGGCACCAAGTTT

3:      I   K   K   E   E   I   E   N   L   Q   K   Y   H   D   I   I   S   R   P   S
        ACATCAAGAAAGAGGAAATTGAAAACTTACAAAAGTATCATGATATCATCAGTAGGCCTT
1441    ---------!---------!---------!---------!---------!---------! 1500
        TGTAGTTCTTTCTCCTTTAACTTTTGAATGTTTTCATAGTACTATAGTAGTCATCCGGAA

3:      H   I   F   R   L   C   N   D   L   A   S   A   S   A   E   I   A   R   G   E
        CCCACATCTTTCGTCTTTGCAACGACCTGGCTTCAGCATCGGCTGAGATAGCGAGAGGTG
1501    ---------!---------!---------!---------!---------!---------! 1560
        GGGTGTAGAAAGCAGAAACGTTGCTGGACCGAAGTCGTAGCCGACTCTATCGCTCTCCAC

3:      T   A   N   S   V   S   C   Y   M   R   T   K   G   I   S   E   E   L   A   T
        AAACTGCGAATTCCGTATCCTGCTACATGCGTACAAAAGGCATTTCTGAGGAACTTGCTA
1561    ---------!---------!---------!---------!---------!---------! 1620
        TTTGACGCTTAAGGCATAGGACGATGTACGCATGTTTTCCGTAAAGACTCCTTGAACGAT

3:      E   S   V   M   N   L   I   D   E   T   C   K   K   M   N   K   E   K   L   G
        CTGAATCCGTAATGAATTTGATCGACGAAACCTGTAAAAAGATGAACAAAGAAAAGCTTG
1621    ---------!---------!---------!---------!---------!---------! 1680
        GACTTAGGCATTACTTAAACTAGCTGCTTTGGACATTTTTCTACTTGTTTCTTTTCGAAC

3:      G   S   L   F   A   K   P   F   V   E   T   A   I   N   L   A   R   Q   S   H
        GTGGCTCTTTGTTTGCAAAACCTTTTGTCGAAACAGCTATTAACCTTGCACGGCAATCCC
1681    ---------!---------!---------!---------!---------!---------! 1740
        CACCGAGAAACAAACGTTTTGGAAAACAGCTTTGTCGATAATTGGAACGTGCCGTTAGGG

3:      C   T   Y   H   N   G   D   A   H   T   S   P   D   E   L   T   R   K   R   V
        ATTGCACTTATCATAACGGAGATGCGCATACTTCACCAGACGAGCTAACTAGGAAACGTG
1741    ---------!---------!---------!---------!---------!---------! 1800
```

FIGURE 6F

```
                TAACGTGAATAGTATTGCCTCTACGCGTATGAAGTGGTCTGCTCGATTGATCCTTTGCAC [SEQ ID NO: 15]

3:    L  S  V  I  T  E  P  I  L  P  F  E  R  *  [SEQ ID NO: 14]
             TCCTGTCAGTAATCACAGAGCCTATTCTACCCTTTGAGAGATAAAAGTAACAGGTTTTCC
      1801   ----------|----------|----------|----------|----------|----------|   1860
             AGGACAGTCATTAGTGTCTCGGATAAGATGGGAAACTCTCTATTTTCATTGTCCAAAAGG

ATGTTGTCGTCTGCAAGAACAAATAACATATGCTGCGTAGAAAATTAAGCCATGTAAATA
      1861   ----------|----------|----------|----------|----------|----------|   1920
             TACAACAGCAGACGTTCTTGTTTATTGTATACGACGCATCTTTTAATTCGGTACATTTAT

GGCTTTAACTCCATGTCGGCGGAGTTTTTGCAGCAGCAAGTACCCTCCTGTATTGTGGA
      1921   ----------|----------|----------|----------|----------|----------|   1980
             CCGAAATTGAGGTACAGCCGCCTCAAAAACGTCGTCGTTCATGGGAGGACATAACACCT

TGGAGAGTATTGTATATTTTCATTCAGATTACAAGGAAGATTATATATCCATTTCTTAT
      1981   ----------|----------|----------|----------|----------|----------|   2040
             ACCTCTCATAACATATAAAAGTAAGTCTAATGTTCCTTCTAATATATAGGTAAAGAATA

TTTCAGTGCAAAAAAAAAAAAA  [SEQ ID NO: 13 cont.]
      2041   ----------|----------|---   2062
             AAACTCACGTTTTTTTTTTTTT  [SEQ ID NO: 15 cont.]
```

FIGURE 6G

ATGGCAACTGAATTATTGTGCTTGCACCGTCCAATCTCACTGACACACAAA [SEQ ID NO:17]
CTGTTCCGAAATCCCTTACCTAAAGTCATCCAGGCCACTCCCTTAACTTTG
AAACTCCGATGTTCTGTAAGCACAGAAAACGTCAGCTTCACAGAAACAGA
ACAGAAGCCCGACGGTCTGCCAATTATGAACCAAATAGCTGGGATTATG
ATTTTTTGCTGTCTTCAGACACTGACGAATCGATTGAAGTATACAAAGACA
AGGCCAAAAAGCTGGAGGCTGAGGTGCGACGAGAGATTAACAATGAAAA
GGCAGAGTTTTTGACTCTGCTTGAACTGATTGATAATGTCCAAAGGTTAGG
ATTGGGTTACCGGTTCGAGAGTGACATTAGGCGAGCCCTCGACCGATTTG
TTTCTTCAGGAGGATTTGATGGTGTTACAAAAACTAGCCTTCATGCTACTG
CTCTTAGCTTCAGGCTTCTCCGACAGCATGGCTTTGAGGTCTCTCAAGAAG
CGTTCAGTGGATTCAAGGATCAAAATGGCAATTTCTTGGAAAACCTTAAG
GAGGACACCAAGGCAATTCTAAGCCTATATGAAGCCTCATTTCTTGCATTA
GAAGGAGAAAATATCTTGGATGAGGCCAGGGTGTTTGCAATTTCACATCT
AAAAGAGCTCAGCGAAGAAAGATTGGAAAAGAGCTGGCCGAACAGGTG
AATCATGCATTGGAGCTTCCATTGCATCGCAGGACGCAACGACTAGAAGC
TGTTTGGAGTATTGAAGCATACCGTAAAAAGGAAGATGCAAATCAAGTAC
TGCTAGAACTTGCTATTTTGGACTACAACATGATTCAATCAGTATACCAAC
GTGATCTTCGTGAGACATCAAGGTGGTGGAGGCGAGTGGGTCTTGCAACA
AAGTTGCATTTTGCTAAAGACAGGTTAATTGAGAGCTTTTACTGGGCAGTT
GGAGTTGCGTTCGAACCTCAATACAGTGATTGCCGTAATTCAGTAGCAAA
AATGTTTTCATTTGTAACAATCATTGATGATATCTATGATGTTTATGGTACT
CTGGATGAGCTGGAGCTATTTACAGATGCTGTTGAGCGATGGGATGTTAA
CGCCATCAATGATCTTCCGGATTATATGAAGCTCTGCTTCCTAGCTCTCTA
CAACACTATCAATGAGATTGCTTATGACAATCTGAAGGACAAGGGGGAAA
ACATTCTTCCATACCTAACAAAAGCGTGGGCAGATTTATGCAATGCATTCC
TACAAGAAGCAAAATGGCTGTACAATAAGTCCACACCAACATTTGATGAC
TATTTCGGAAATGCATGGAAATCATCCTCAGGGCCTCTTCAACTAATTTTT
GCCTACTTTGCCGTGGTTCAAAACATCAAGAAAGAGGAAATTGAAAACTT
ACAAAAGTATCATGATATCATCAGTAGGCCTTCCCACATCTTTCGTCTTTG
CAACGACCTGGCTTCAGCATCGGCTGAGATTGCACGAGGTGAAACTGCCA
ATTCCGTATCCTGCTACATGCGTACAAAAGGCATTTCTGAGGAACTTGCTA
CTGAATCCGTAATGAATTTGATCGACGAAACCTGGAAAAAGATGAACAAA
GAAAAGCTCGGTGGCTCTTTGTTTGCAAAACCTTTTGTCGAAACAGCTATT
AACCTTGCACGGCAATCCCATTGCACTTATCATAACGGAGATGCGCATAC
TTCACCAGACGAGCTAACTAGGAAACGTGTCCTGTCAGTAATCACAGAGC
CTATTCTACCCTTTGAGCGATAA

METHODS FOR THE DIRECT CONVERSION OF CARBON DIOXIDE INTO A HYDROCARBON USING A METABOLICALLY ENGINEERED PHOTOSYNTHETIC MICROORGANISM

RELATED APPLICATIONS

This application claims the benefit of provisional application 60/927,102 filed May 1, 2007 entitled "Methods for the Direct Conversion of Carbon Dioxide Into A Hydrocarbon Using a Metabolically Engineered Photosynthetic Microorganism," and PCT/2008/005707, filed May 1, 2008, entitled the same, and incorporate teachings in their entirety by reference.

BACKGROUND OF THE INVENTION

One of the greatest challenges for society in the 21$^{st}$ century is to meet the growing demand for energy for transportation, heating and industrial processes, and to provide the raw materials for the industry in a sustainable way. More importantly, the future energy and raw materials supply must be met with a simultaneous substantial reduction of green house gas emissions. The oil, gas, and coal industries have dominated not only the energy market for the past 80 years but also the carbon-based chemicals industry. Declining crude oil reserves, political unrest and increasing global demand of oil and its refinery products (petro-derived chemicals aka petrochemicals), which form the basis for the industrial chemicals sector have driven up the cost of energy as well as these key hydrocarbon derivatives and their downstream products. Further, the combustion and refinement of fossil fuels has sparked concerns regarding the effects of greenhouse gas emissions on global warming. Incited by concerns for the environment and recent advances in biotechnological research synthetic biology techniques can now be applied to engineering of microbes to enable biosynthetic (renewable) manufacture of important raw materials for the chemical industry. At present the production of ethanol as a liquid biofuel from renewable plant resources is the principal approach being taken.

Ethanol has already been introduced on a large scale in Brazil, the US and some European countries. Ethanol can be blended with petrol or used as neat alcohol in dedicated engines. Currently, ethanol for the fuel market is produced from sugar (Brazil) or starch (USA). The production of ethanol from starch-containing materials requires a liquefaction step (to make starch soluble) and a hydrolysis step (to produce glucose). The resulting glucose is readily fermented. However, this raw material base, which also is used for animal feed and human needs, will not be sufficient to meet the increasing demand for fuel ethanol; and the reduction of greenhouse gases resulting from the use of sugar or starch-based ethanol is not as high as desirable (Farrell et al., 2006).

To address both these limitations, the exploitation of lignocellulose feedstocks, such as agricultural and forest residues as well as dedicated crops, for the production of ethanol, has been explored. There are many techno-economic challenges facing the lignocellulose-to-ethanol process, reviewed in (Hahn-Hagerdal et al., 2006).

First, cellulose and hemi-cellulose have to be de-polymerized into soluble sugars by biodegradation. Enzyme conversion is substrate specific without by-product formation, which reduces inhibition of the following processes. However, enzyme catalyzed conversion of cellulose to glucose is slow unless the biomass has been subjected to pretreatment, which is also required to reach high yields and to make the process commercially successful (Mosier et al., 2005).

Second, the de-polymerization of cellulose produces a mixed-sugar hydrolysate containing six-carbon (hexoses) and five-carbon (pentoses) sugars which have to be efficiently fermented into ethanol, as well as fermentation inhibitory compounds—low molecular weight organic acids, furan derivatives, phenolics and inorganic compounds released and formed during pretreatment and/or hydrolysis of the raw material (Larsson et al., 2000). Lignocellulosic raw materials, in particular hardwood and agricultural raw materials, can contain 5-20% (or more) of the pentose sugars xylose and arabinose, which are not fermented to ethanol by the most commonly used industrial fermentation microorganism, the yeast Saccharomyces cerevisiae. Pentose fermenting microorganisms have been genetically engineered and methods are being developed to remove toxic inhibitors using chemical or physical methods, reviewed in (Hahn-Hagerdal et al., 2006).

Third, to minimize process energy demands, advanced processes to integrate de-polymerization of cellulose and fermentation of the resultant sugars must be developed. Two approaches have been taken: separate hydrolysis and fermentation (SHF) and simultaneous saccharification and fermentation of cellulose (SSF). In SHF, cellulose is first hydrolyzed to glucose and then glucose is fermented to ethanol. The primary advantage of SHF is that hydrolysis and fermentation occur at optimum conditions; the disadvantage is that cellulolytic enzymes are end-product inhibited so that the rate of hydrolysis is progressively reduced when glucose and cellubiose accumulate (Tengborg et al., 2001). In SSF, hydrolysis and fermentation occur simultaneously in the same vessel, and the end-product inhibition of the enzymes is relieved because the fermenting organism immediately consumes the released sugars. Furthermore, the fermentation seems to decrease the inhibition of enzymes by converting some of the toxic compounds present in the hydrolysate (Tengborg et al., 2001). This increases the overall ethanol productivity, the ethanol concentration and the final ethanol yield (Söderström et al., 2005).

For all the excitement surrounding the production and use of ethanol as a biofuel, there are a number of weaknesses to this approach. There is a need for methods to produce hydrocarbons that can be used as fuel more efficiently than ethanol. These methods also need to provide a means for substantially reducing green house gases.

SUMMARY OF THE INVENTION

The present invention relates to genetically engineered photosynthetic microorganisms, such as cyanobacteria, that are capable of producing hydrocarbons such as isoprene from carbon dioxide ($CO_2$). The present invention also relates to methods for the production of isoprene, by the direct conversion of carbon dioxide using genetically engineered photosynthetic microorganisms (also referred to as metabolically engineered photosynthetic microorganisms).

One embodiment of the invention is a photosynthetic microorganism, such as cyanobacterium, that has been genetically engineered to produce a hydrocarbon compound (also referred to as a hydrocarbon) that is substantially immiscible in water. In some embodiments, the hydrocarbon compound can be in the form of a gas, an immiscible liquid or a precipitable. In some embodiments, the hydrocarbon is isoprene, and the photosynthetic microorganism (e.g., genetically engineered cyanobacterium) produces isoprene when it is cultured in the presence of carbon dioxide. In some embodiments, the carbon dioxide is atmospheric carbon dioxide. In some embodiments, the cyanobacteria is cultured in the presence of carbon dioxide generated from a fossil fuel plant or a smokestack (scrubber). In some embodiments, the genetically engineered photosynthetic microorganism produces isoprene from precursors generated via the 2-C-methyl-D-erythritol-4-phosphate metabolic pathway. A wide variety of cyanobacteria can be genetically modified using methods described herein and/or methods known in the art. In one embodiment, the genetically engineered photosynthetic microorganism is a thermophilic cyanobacterium, such as *Thermosynechococcus (T.) elongatus* BP-1. In some embodiments the cyanobacteria is of the genus *Anabaena*. In certain embodiments the cyanobacteria is *Anabaena* 7120.

Aspects of the invention relate to photosynthetic microorganisms, such as cyanobacteria (e.g., a thermophilic cyanobacterium; *T. elongatus* BP-1; a member of the genus *Anabaena*; *Anabaena* 7120) that are genetically engineered through the introduction of a gene encoding isoprene synthase. The encoded isoprene synthase can be from any source, provided that it is functional (exhibits activity) in the genetically engineered microorganism (e.g., cyanobacterium) into which it is introduced. Sources include plants, bacteria, viruses, other nonmammalian sources and mammalian sources. In a particular embodiment, the isoprene synthase gene is a plant isoprene synthase gene, such as a tree isoprene synthase gene. In one embodiment, the isoprene synthase gene is a poplar (*Populus alba×Populus tremula*) isoprene synthase gene. The isoprene synthase gene can be modified, before or after introduction into cyanobacteria, for optimization of expression and/or enzymatic activity in cyanobacteria. In one embodiment, the gene encoding isoprene synthase is integrated into the cyanobacterial genome, while in another embodiment the gene encoding isoprene synthase is carried on a plasmid contained in the genetically engineered photosynthetic microorganism (cyanobacterium).

Aspects of the invention relate to culturing the genetically engineered photosynthetic microorganism, such as genetically engineered cyanobacteria, in a container and in the presence of carbon dioxide and collecting isoprene from the off-gas of the culture of the genetically engineered photosynthetic microorganism. In one embodiment, the genetically engineered cyanobacteria is further modified by the insertion of at least one gene encoding a natural or synthetic enzyme that can utilize isoprene as a substrate for further biosynthesis.

In one embodiment, the invention relates to a genetically engineered photosynthetic microorganism that comprises an exogenous gene that encodes isoprene synthase, wherein the genetically engineered photosynthetic microorganism is capable of producing isoprene from carbon dioxide, such as when the genetically engineered photosynthetic microorganism is cultured in the presence of carbon dioxide. In one embodiment the genetically engineered photosynthetic microorganism is a cyanobacterium, such as *Thermosynechococcus elongatus* BP-1. In some embodiments the cyanobacteria is of the genus *Anabaena*, such as *Anabaena* 7120. In one embodiment, the gene that encodes isoprene synthase is a plant (e.g., tree, flower, shrub, grass) isoprene synthase gene, such as poplar (*Populus alba×Populus tremula*) isoprene synthase gene. In an alternative embodiment, the photosynthetic microorganism is one which, in the absence of modification, produces no/substantially no isoprene and has been genetically engineered in such a manner that a normally silent endogenous isoprene synthase gene is activated, with the result that it functions to produce isoprene.

In one embodiment, the invention relates to a genetically engineered photosynthetic microorganism, such as a cyanobacterium containing an exogenous isoprene synthase gene that has been modified, before or after introduction into cyanobacteria, in order to optimize expression and/or enzymatic activity in cyanobacteria. In one embodiment, the cyanobacterium contains the exogenous gene encoding isoprene synthase integrated into the genome of the cyanobacterium, while in another embodiment the gene encoding isoprene synthase is carried on a plasmid.

Aspects of the invention relate to a genetically engineered photosynthetic microorganism, such as a genetically engineered photosynthetic microorganism (e.g., a genetically engineered cyanobacterium), that is cultured in a container and in the presence of carbon dioxide, allowing for the collection of isoprene from the off-gas of the culture of the cyanobacteria. In one embodiment, the genetically engineered photosynthetic microorganism is further modified by the insertion of at least one gene encoding a natural or a synthetic enzyme that can utilize isoprene as a substrate for further biosynthesis.

Aspects of the invention relate to methods for the production of isoprene through culturing a photosynthetic microorganism that has been genetically engineered to produce isoprene, and, optionally, collecting isoprene produced from the photosynthetic microorganism that has been genetically engineered to produce isoprene. The genetically engineered photosynthetic microorganism is cultured in the presence of carbon dioxide and under conditions appropriate for growth and/or maintenance of the genetically engineered photosynthetic microorganism (e.g., in the presence of sufficient light). In one embodiment, the genetically engineered photosynthetic microorganism is a cyanobacterium, such as *Thermosynechococcus elongatus* BP-1. In some embodiments, the cyanobacteria is of the genus *Anabaena*, such as *Anabaena* 7120. Culture conditions include sufficient light for maintenance and/or growth of the cyanobacterium.

In one embodiment of the method for the production of isoprene, a photosynthetic microorganism, such as a cyanobacterium, that has been genetically engineered to produce isoprene through the introduction of a gene encoding isoprene synthase is used. In one embodiment, the cyanobacterium has been genetically engineered to comprise an isoprene synthase gene from a plant, such as a tree poplar (e.g., *Populus alba×Populus tremula*) isoprene synthase gene. The gene can be from another type of tree or plant (e.g., flower, shrub, grass).

In one embodiment, the method comprises use of cyanobacteria in which the isoprene synthase gene was modified, before or after its introduction into cyanobacteria, in order to optimize expression and/or enzymatic activity in cyanobacteria. In one embodiment, the isoprene synthase gene is integrated into the genome of the genetically engineered photosynthetic microorganism. In another embodiment, the gene encoding isoprene synthase is carried on a plasmid.

Aspects of the invention relate to methods of culturing the genetically engineered photosynthetic microorganism in a container and in the presence of carbon dioxide and, optionally, collecting the isoprene from the off-gas of the culture of the photosynthetic microorganism (e.g., off-gas of the culture of the genetically engineered cyanobacteria). In one embodiment, the method relates to co-culturing the genetically engineered photosynthetic microorganism with one or more additional natural and/or modified microorganisms that can utilize isoprene as a substrate for further biosynthesis.

Aspects of the invention relate to methods for the production of isoprene, comprising culturing a genetically engineered photosynthetic microorganism that comprises an exogenous gene that encodes isoprene synthase, wherein the genetically engineered photosynthetic microorganism is capable of producing isoprene from carbon dioxide and, optionally, collecting isoprene produced from the genetically engineered photosynthetic microorganism that comprises the exogenous gene that encodes isoprene synthase. The genetically engineered photosynthetic microorganism is cultured in the presence of carbon dioxide and under conditions appropriate for growth and/or maintenance (e.g., in the presence of sufficient light). In one embodiment, cyanobacteria, such as The *Thermosynechococcus elongatus* BP-1, is used. In some embodiments the cyanobacteria is of the genus *Anabaena*, such as *Anabaena* 7120.

In one embodiment, the exogenous gene encoding isoprene synthase is a plant gene such as poplar (*Populus alba*×*Populus tremula*) isoprene synthase gene. In one embodiment, the method for producing isoprene includes modification of the isoprene synthase gene, before or after introduction into cyanobacteria, in order to optimize expression and/or enzymatic activity of isoprene synthase in cyanobacteria. In one embodiment, the gene encoding isoprene synthase is integrated into the genome of the genetically engineered photosynthetic microorganism (e.g., the cyanobacteria), and in another embodiment, it is carried on a plasmid in the microorganism.

Aspects of the invention relate to methods for producing isoprene by culturing the genetically engineered photosynthetic microorganism in a container in the presence of carbon dioxide and, optionally, collecting the isoprene from the off-gas of the culture of the genetically engineered photosynthetic microorganism. In one embodiment, the genetically engineered photosynthetic microorganism is co-cultured in a container in the presence of carbon dioxide, with one or more additional natural and/or modified microorganisms that are capable of utilizing isoprene as a substrate for further biosynthesis.

Aspects of the invention relate to optimization of a genetically engineered photosynthetic microorganism for isoprene production and optimization of methods for producing isoprene from a photosynthetic microorganism. In some embodiments, the amount of isoprene production is improved by altering the expression level and control of isoprene synthase expression in the genetically engineered photosynthetic microorganism. In other embodiments, the amount of isoprene production is improved by altering the coding region for the isoprene synthase gene in the genetically engineered photosynthetic microorganism, through protein engineering techniques to improve the thermostability, specific activity and specificity of the isoprene synthase gene. In other embodiments, the amount of isoprene production is improved by over-expression and/or intrinsic activity ($k_{cat}/K_m$) enhancement in the genetically engineered photosynthetic microorganism, of enzymes upstream of isoprenenyl diphosphate or dimethylallyl diphosphate synthesis that are known to be limiting. In other embodiments, the amount of isoprene production is improved by random mutagenesis (with transposon or transposon-like insertions or with standard mutagenesis) in the genetically engineered photosynthetic microorganism and screening for improved organism production. In other embodiments, the amount of isoprene production is improved by shotgun cloning of genome fragments from the same or related organisms, followed by screening for improved organism production, to identify cryptic pathways that can be added or enhanced by over-expressing factors in trans. In certain embodiments, the amount of isoprene production is improved by combining multiple mutations in a single organism.

In some embodiments, optimization of a genetically engineered photosynthetic microorganism for the production of isoprene, or optimization of methods for producing isoprene from a genetically engineered photosynthetic microorganism will be further achieved through culturing a genetically engineered photosynthetic microorganism in which the amount of isoprene production has been improved in a microbial bioreactor and optimizing culture protocols in the microbial bioreactor. In some embodiments, optimization of a genetically engineered photosynthetic microorganism for the production of isoprene, or optimization of methods for producing isoprene from a genetically engineered photosynthetic microorganism will be further achieved through optimization of harvesting protocols to collect isoprene from the microbial bioreactor.

According to another aspect of the invention, a nucleic acid molecule is provided. The nucleic acid molecule comprises the nucleic acid sequence of modified isoprene synthase gene (v2.2.1).

In some embodiments, an expression vector comprising nucleic acid sequence of modified isoprene synthease gene (v2.2.1) operably linked to a promoter is provided. In a related aspect, host cells transformed or transfected with such expression vectors also are provided.

According to another aspect of the invention, an isolated polypeptide or a variant thereof is provided. The isolated polypeptide is encoded by the nucleic acid sequence of modified isoprene synthease gene (v2.2.1).

BRIEF DESCRIPTION OF THE DRAWINGS

FIGS. 3A-3E. The amino acid and nucleic acid sequence of the isoprene synthase gene isolated from poplar leaves (Miller et al., 2001).

FIGS. 4A-4B. Alignment of four isoprene synthase sequences from the genus *Populus*.

FIGS. 6A-6G. The nucleic acid sequence of synthetic isoprene synthase gene (v2.2) and of synthetic isoprene synthase gene.

FIG. 7. Nucleic acid sequence of modified isoprene synthase gene (v2.2.1).

DETAILED DESCRIPTION OF THE INVENTION

Aspects of the invention relate to methods and compositions for producing isoprene from $CO_2$ through genetic engineering of a photosynthetic microorganism. Genetically engineered photosynthetic microorganisms such as cyanobacteria synthesize the penultimate isoprene precursors: isopentenyl diphosphate and dimethylallyl diphosphate via the 2-C-methyl-D-erythritol-4-phosphate pathway, but lack a gene encoding for isoprene synthase, which in plants performs the final step in the biosynthesis of isoprene from its precursors. Like plants, cyanobacteria are autotrophic: the ultimate carbon source for isopentenyl diphosphate and dimethylallyl diphosphate in the presence of light is photosynthetic fixation of atmospheric $CO_2$. Hence a cyanobacterium, metabolically engineered to incorporate an expressible isoprene synthase gene, could generate isoprene directly from carbon dioxide and water in the presence of light.

Isoprene is a volatile compound with a boiling point of 34° C. and can be harvested from the off-gas of a bacterial fermentation by a simple condensation. In terms of maximizing isoprene production from a genetically engineered microorganism this volatility is an extremely attractive feature, since the product is continuously removed from the culture and thus never accumulates to become the limiting factor (product inhibition). An isoprene product stream from a photosynthetic bacterial culture would be a valuable starting material for industrial synthesis of gasoline additives/replacements and a novel form of "biofuel." Although multiple industrial synthetic routes to such an additive can be imagined, one such route is given as an example below.

Figure 1:
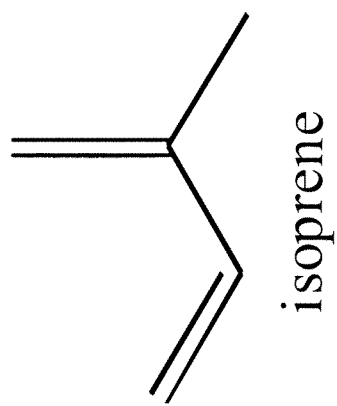
FIG. 1. Illustrates the structure and physical properties of Isoprene.
Figure 2:
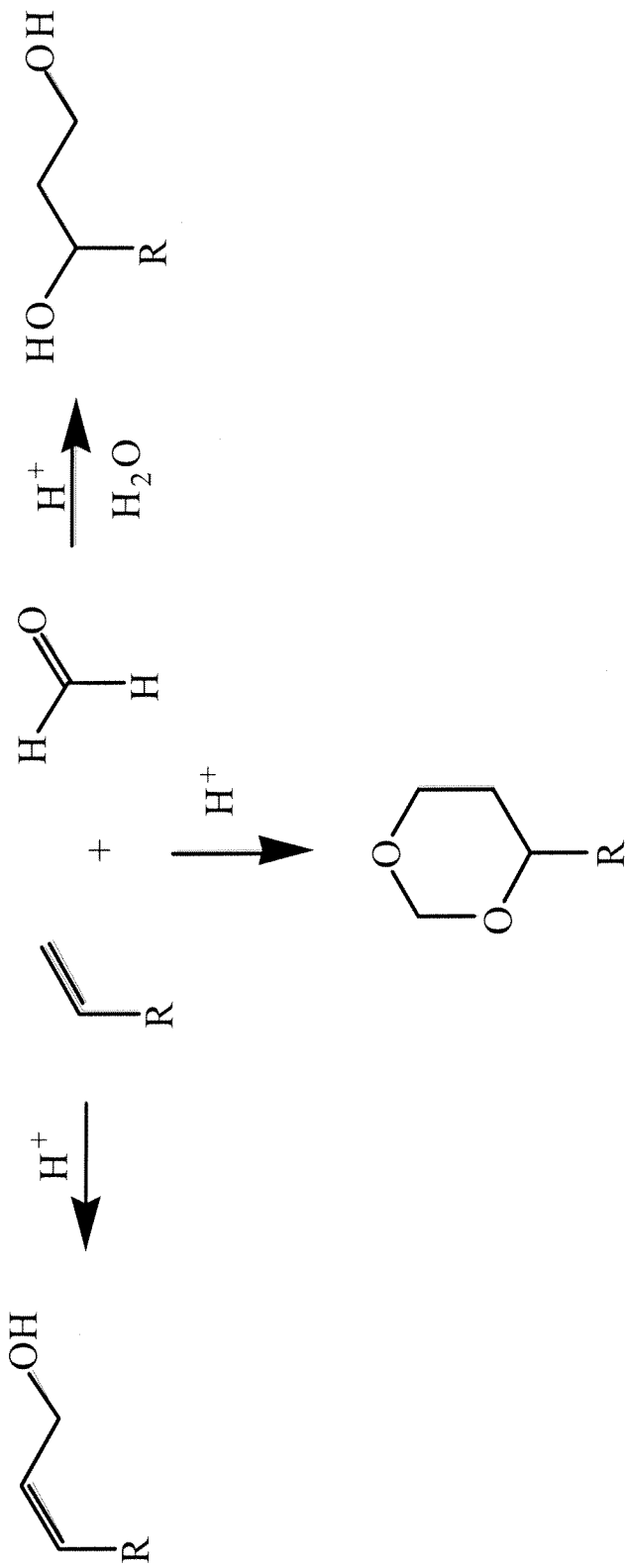
FIG. 2. The Prins reaction. In the scheme shown, the aldehyde added is formaldehyde. Use of acetaldehyde instead would result in methyl substitutions at the 2 and the 6 positions.
Figure 5:
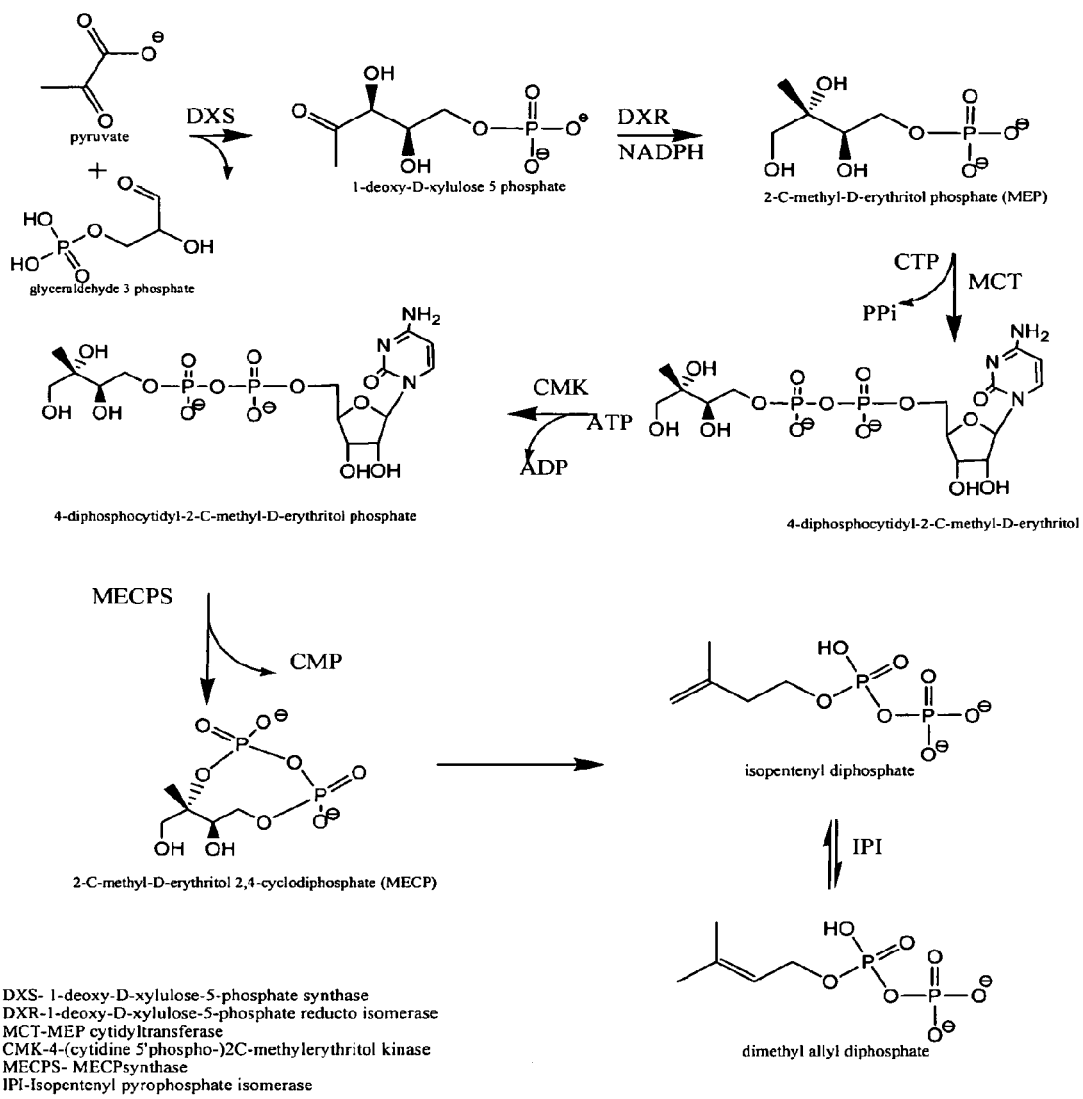
FIG. 5. The MEP pathway in cyanobacteria illustrating the synthetic scheme and key enzymes involved in the production of isopentenyl diphosphate (IPP) and its isomer dimethylallyl diphosphate (DMAPP). Cyanobacteria lack the enzyme isoprene synthase that is responsible for conversion of IPP and DMAPP to isoprene. Abbreviations are as follows: DXS, 1-deoxy-D-xylulose-5-phosphate synthase; DXR, 1-deoxy-D-xylulose-5-phosphate reductoisomerase; MCT, MEP cytidyltransferase; CMK, 4-(cytidine 5' phospho-)2C-methylerythritol kinase; MECPS, MECP synthase; IPI, isopentenyl diphosphate isomerase.

Isoprene can be mixed with a suitable aldehyde (including acetaldehyde derived from cellulosic ethanol) and an appropriate catalyst in a reactor, and converted by an aqueous Prins reaction into an alkyl substituted 1,3-dioxane in high yield (Arundale and Mikeska, 1952; FIG. 2, compound 5). Potentially, the 1,3-dioxane products could be harvested continuously from the reactor by a simple phase separation and, with only minor further refinement, used directly as gasoline additives. Various 1,3-dioxanes have boiling points that endow them with high octane numbers and can be blended with gasoline in ratios as high as 50:50 (v/v) to produce fuel for internal combustion engines (Arundale and Mikeska, 1952). 1,3-dioxane additives also create cleaner burning gasoline blends, thereby reducing engine deposits and hydrocarbon emissions that contribute to air pollution (Niebylski, 1980). 1,3-dioxane is a cyclic ether, and there is over a decade of experience in the oil industry handling ethers such as MTBE (methyl tertiary-butyl ether) as gasoline additives, so potential problems (e.g., peroxide build up over time) have already been addressed.

This invention provides methods and compositions for metabolically engineering a photosynthetic microorganism to express isoprene synthase. It further provides methods for the collection of isoprene through culturing the metabolically engineered photosynthetic microorganism in the presence of carbon dioxide.

Aspects of the invention relate to the use of genetically engineered photosynthetic microorganisms. In one embodiment the genetically engineered photosynthetic microorganism is a cyanobacterium. The isoprene synthase precursors, isopentenyl diphosphate and dimethylallyl diphosphate, are synthesized in all known cyanobacteria (Cunningham, Jr. et al., 2000; Ershov et al., 2002; Okada and Hase, 2005). Thus, the cyanobacterium used could be selected from, but is not limited to, the following members of cyanobacteria genera (Castenholz, 2001): Subsection I: *Chamaesiphon, Chroococcus, Cyanobacterium, Cyanobium, Cyanothece, Dactylococcopsis, Gloeobacter, Gloeocapsa, Gloeothece, Microcystis, Prochlorococcus, Prochloron, Synechococcus, Synechocystis*, Subsection II: *Cyanocystis, Dermocarpella, Stanieria, Xenococcus, Chroococcidiopsis, Myxosarcina, Pleurocapsa*, Subsection III: *Arthrospira, Borzia, Crinalium, Geitlerinema, Halospirulina, Leptolyngbya, Limnothrix, Lyngbya, Microcoleus, Oscillatoria, Planktothrix, Prochlorothrix,* *Pseudanabaena, Spirulina, Starria, Symploca, Trichodesmium, Tychonema*, Subsection IV: *Anabaena, Anabaenopsis, Aphanizomenon, Calothrix, Cyanospira, Cylindrospermopsis, Cylindrospermum, Nodularia, Nostoc, Rivularia, Scytonema, Tolypothrix*, Subsection V: *Chlorogloeopsis, Fischerella, Geitleria, Iyengariella, Nostochopsis, Stigonema* (http://tolweb.org/tree?group=Cyanobacteria; Castenholz, 2001). The nomenclature for cyanobacteria is under revision (Oren, 2004).

In one embodiment, the species of cyanobacteria used is selected from species that are adapted for growing at higher temperatures, including but not limited to, *Thermosynechococcus elongatus* BP-1 (*T. elongatus*) and thermo-tolerant strains of the genus *Synechococcus* (Miller and Castenholz, 2000; Yamaoka et al., 1978). In another embodiment, the strain of cyanobacteria used is selected from species that have been shown to naturally take up exogenous DNA, including but not limited to *Gloeocapsa alpicola, Agmenellum quadruplicatum, Anacystis nidulans, Synechocystis* sp. PCC 6803, and *Thermosynechococcus elongatus* BP-1 (Grigorieva and Shestakov, 1982; Onai et al., 2004; Szalay and Williams, 1988). In another embodiment, the strain of cyanobacteria used is selected from species for which electroporation has been shown to be an effective method of introducing foreign DNA, including but not limited to *Anabaena* sp. M131, *Fremyella diplosiphon, Nostoc* PCC 7121, *Chroococcidiopsis* sp., *Spirulina platensis* C1, *Oscillatoria* MKU 277, and *Thermosynechococcus elongatus* BP-1 (Billi et al., 2001; Bruns et al., 1989; Iwai et al., 2004; Kawata et al., 2004; Moser et al., 1993; Ravindran et al., 2006; Thiel and Poo, 1989).

In some embodiments, the cyanobacteria is of the genus *Anabaena*. In certain embodiments the cyanobacteria is *Anabaena* 7120.

Aspects of the invention relate to genetic engineering of a photosynthetic microorganism. In one embodiment this relates to the introduction of a gene encoding isoprene synthase into the genetically engineered photosynthetic microorganism. In one embodiment the gene encoding isoprene synthase is a plant gene, including but not limited to, a gene from the poplar (*Populus alba×Populus tremula*).

Aspects of the invention relate to the expression of an exogenous gene encoding isoprene synthase in a genetically engineered photosynthetic microorganism such as cyanobacteria. In certain embodiments, the isoprene synthase gene is integrated into the chromosome of the cyanobacteria. In other embodiments, the isoprene synthase gene is expressed on a plasmid. The isoprene synthase gene may be introduced into cyanobacteria by standard methods known to those of skill in the art. This could include, but is not limited to, standard protocols for transformation including chemical transformation and electroporation, and standard protocols for interspecies conjugation and chromosomal recombination (Tsinoremas et al., 1994; Muhlenhoff and Chauvat, 1996)). One form of transformation involves creating a plasmid that comprises the foreign (exogenous) gene or genes of interest inserted between two flanking portions of DNA that represent sequences that are adjacent in the chromosome of the recipient cyanobacterial cell. The length of the flanking portions of recipient chromosomal DNA should each be at least 100 bp (Szalay and Williams, 1988). Suitable sites for chromosomal insertion can be chosen randomly from a shotgun library of chromosomal fragments followed by screening of insertant colonies for those that exhibit robust growth or other desired phenotype (Szalay and Williams, 1988). Alternatively, insertion can be done at specific sites using PCR or another method to isolate a particular region of chromosomal DNA in which to target the insertion (Iwai et al., 2004). Constructs that promote either double crossing-over (insertion with gene replacement) or single crossing-over (insertion with partial gene duplication) events (ibid.) are made. Incorporation of antibiotic resistance markers along with the gene(s) of interest in the inserted DNA allows for selection of transformants.

In one embodiment of the invention, plasmids are used for expression of the isoprene synthase gene. Plasmid vectors either can replicate in one's host of choice, or cannot. Each type of behavior has experimental uses. Replicating vectors can potentially express an exogenous gene in a new host. Such vectors may have either broad or narrow host range. Derivatives of plasmid RSF1010, for example, are capable of replicating in *Synechocystis* (Marraccini et al., 1994; Mermet-Bouvier et al., 1993) as well as in *Anabaena* 7120 (Thiel, 1994), *Synechococcus* (including a thermophilic strain) and *Pseudanabaena* (Muhlenhoff and Chauvat, 1996; Sode et al., 1992), and warrant testing for replication in a strain new to genetic analysis. In contrast, plasmids based on the 6.3-kb plasmid pDUI from *Nostoc* 7524 can replicate in several Section-IV strains (sensu (Rippka et al., 1979); Table 1) and a Section-II strain (Billi et al., 2001), but have not been reported to replicate in Section-I strains. Plasmid vectors that can be transferred to, but cannot replicate in, a new host are ideal for transporting DNA that must either transpose (e.g., a transposon, used for mutagenesis) or integrate (e.g., by homologous recombination) in order to be stably maintained. Thiel (1994) has described a variety of each for cyanobacteria.

Aspects of the invention relate to the expression of a gene encoding isoprene synthase in cyanobacteria. In some embodiments the gene encoding isoprene synthase is a plant gene. Many genetic tools are available for cyanobacteria (reviewed in Koksharova and Wolk, 2002) and thus many options exist for optimizing expression of isoprene synthase in cyanobacteria. The isoprene synthase gene may be modified before being introduced into cyanobacteria. In one embodiment, this would involve modifying the sequence to provide optimized codons for expression in a species of cyanobacteria such as *T. elongatus* or *Anabaena* 7120. Total gene synthesis allows encoding proteins using one genetic code to be expressed in a host organism that utilizes a different genetic code. One does this by designing the synthetic genes so that the appropriate host codons are used for each amino acid position in the desired protein where the codes differ. Thus, when the message transcribed from the synthetic gene is translated in the recombinant host, a polypeptide will be produced having the same amino acid sequence as would the protein expressed in its natural host. By the same token, desired mutations can be deliberately engineered into the designed gene (and protein) using the host's genetic code to guide the selection of appropriate nucleotide substitutions, deletions, or insertions. In one embodiment, codon usage optimization would be based on the genetic code and codon usage table for the cyanobacterial strains *T. elongatus* BP-1 (Nakamura et al., 2002) or *Anabaena* 7120. Codon usages for many other organisms can be found in the Codon Usage Database (http://www.kazusa.or.jp/codon/).

In another embodiment, optimization of expression in cyanobacteria would relate to avoidance of restriction sites in cyanobacteria. Where genome sequence information is available for cyanobacterial hosts, restriction system subunits encoded by hsdRMS genes (Bickle and Kruger, 1993; Murray, 2000) can be identified by their sequence homology to other bacterial hsdRMS genes. The tll2228, tll2229, and tll2230 genes of *T. elongatus* were recognized by this method, and this information was used to design and construct a strain where the tll2230 gene was disrupted by insertional mutagenesis. This strain exhibited an enhanced transformation efficiency (Iwai et al., 2004). Other evidence of Type II restriction systems in *T. elongatus* includes the presence in cells of a restriction enzyme, Sel I, that cleaves at the sequence CGCG (Miyake et al., 1992) and methylation of the genomic DNA at RGATCY sequences (Kinoshita and Ikeuchi, unpublished observations, cited by Iwai et al. (2004)). With total gene synthesis and by knowing the genetic code of the cyanobacterial host (above), synthetic genes can be constructed that accurately encode proteins of interest yet minimize the use of codons that would result in the presence of CGCG or RGATCY or other restriction sites in the DNA to be transformed.

In another embodiment, optimization of expression in cyanobacteria refers to optimizing transcription initiation in cyanobacteria. Many genes that express well in *E. coli* also express in cyanobacteria. This indicates that the transcriptional control sequences governing expression of these genes are also active in cyanobacteria. For example, the streptomycin/spectinomycin adenylyltransferase gene from plasmid pRL453 and a chloramphencol resistance ($Cm^R$) cassette were found to express effectively in *Thermosynechococcus elongatus* BP-1 (Iwai et al., 2004). The promoter for the *Anacystis nidulans* R2 ferredoxin I gene (petF1) has been isolated and has the sequence (reading 5' to 3', from 120 nucleotides upstream of the ATG start codon; −35 and −10 regions of the promoter and the transcript start site are indicated by underlining):

```
                   -35                         -10         start    [SEQ ID NO: 1]
      TTGATAGCATTTCTCGCGGCGCAGTTCGCCCTTTGGCAACCCATAGTATCAATGGGAAAGG.
```

(Reith et al., 1986). Note that in this particular promoter the −10 box is similar to the *E. coli* consensus sequence but the −35 box is dissimilar. This promoter and the associated petF1 ribosome binding site and initiation codon were fused to a heterologous gene, the *Bacillus thuringiensis* cryIVB gene and used to drive expression of that gene in *Synechococcus* sp. strain PCC 7942 cells transformed with the fusion construct (Soltes-Rak et al., 1993). Similarly, the rbcLS promoter, governing expression of the ribulose-1,5-bisphosphate carboxylase/oxygenase operon in *Anacystis nidulans* 6301, was used to express the pyruvate decarboxylase and alcohol dehydrogenase II genes from *Zymomonas mobilis* in the cyanobacterial host, *Synechococcus* sp. strain PCC 7942 (Deng and Coleman, 1999). Numerous other promoters effective in cyanobacterial expression are known. Human carbonic anhydrase II (HCAII) has been expressed in *Synechococcus* PCC 7942 under control of the hybrid tac promoter and the lacI$^q$ repressor from *E. coli*, allowing regulation of HCAII expression levels by the exogenously added inducer isopropyl-β-D-thiogalactopyranoside (IPTG) (Price and Badger, 1989). Furthermore, the pyruvate decarboxylase and alcohol dehydrogenase II genes from *Zymomonas mobilis*, have been expressed under temperature-inducible control in *Synechococcus* PCC 7942 using the lambdaphage cI $P_L$ promoter under the control of the cI857 temperature-sensitive repressor.

The invention thus involves in one aspect genes encoding isoprene synthase. In some embodiments the isoprene synthase gene is a poplar isoprene synthase gene. It should be appreciated that homologs and alleles of isoprene synthase nucleic acids of the invention can be identified by conventional techniques. Thus, an aspect of the invention is those nucleic acid sequences which code for isoprene synthase enzymes.

In general homologs and alleles typically will share at least 75% nucleotide identity and/or at least 90% amino acid identity to the sequences of isoprene synthase nucleic acid and polypeptides, respectively, in some instances will share at least 90% nucleotide identity and/or at least 95% amino acid identity and in still other instances will share at least 95% nucleotide identity and/or at least 99% amino acid identity. The homology can be calculated using various, publicly available software tools developed by NCBI (Bethesda, Md.) that can be obtained through the NCBI internet site. Exemplary tools include the BLAST software, also available at the NCBI internet site. Pairwise and ClustalW alignments (BLOSUM30 matrix setting) as well as Kyte-Doolittle hydropathic analysis can be obtained using the Mac Vector sequence analysis software (Oxford Molecular Group). Watson-Crick complements of the foregoing nucleic acids also are embraced by the invention.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating isoprene synthase polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules which include additions, substitutions and deletions of one or more nucleotides. In some embodiments, these modified nucleic acid molecules and/or the polypeptides they encode retain at least one activity or function of the unmodified nucleic acid molecule and/or the polypeptides, such as antigenicity, enzymatic activity, formation of complexes, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York.

More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/ 0.15M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of isoprene synthase nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

In some embodiments the modification or mutation made to the nucleic acid does not alter the amino acid sequence of the encoded polypeptide. In some embodiments the modification or mutation made to the nucleic acid alters the amino acid sequence of the encoded polypeptide but does not alter the activity (e.g., functional or physiological activity) of the encoded polypeptide.

The invention embraces variants of the isoprene synthase polypeptides described herein. As used herein, a "variant" of an isoprene synthase polypeptide is a polypeptide which contains one or more modifications to the primary amino acid sequence of an isoprene synthase. Modifications which create an isoprene synthase variant can be made to an isoprene synthase polypeptide for example to enhance a property of an isoprene synthase polypeptide, such as protein stability in an expression system or the stability of protein-protein binding. Modifications to an isoprene synthase polypeptide are typically made to the nucleic acid which encodes the isoprene synthase polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the isoprene synthase amino acid sequence. One of skill in the art will be familiar with methods for predicting the effect on protein conformation of a change in protein sequence, and can thus "design" a variant isoprene synthase polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of an isoprene synthase polypeptide can be proposed and tested to determine whether the variant retains a desired conformation.

In general, variants include isoprene synthase polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of an isoprene synthase polypeptide by eliminating proteolysis by proteases in an expression system (e.g., dibasic amino acid residues in yeast expression systems in which KEX2 protease activity is present).

Mutations of a nucleic acid which encode an isoprene synthase polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant isoprene synthase polypeptides) which are silent as to the amino acid sequence of the polypeptide, but which provide preferred codons for translation in a particular host. Still other mutations can be made to the noncoding sequences of an isoprene synthase gene or cDNA clone to enhance expression of the polypeptide. The activity of variants of isoprene synthase polypeptides can be tested by cloning the gene encoding the variant isoprene synthase polypeptide into an appropriate expression vector, introducing the vector into an appropriate host cell, expressing the variant isoprene synthase polypeptide, and testing for a functional capability of the isoprene synthase polypeptides as disclosed herein. Preparation of other variant polypeptides may favor testing of other activities, as will be known to one of ordinary skill in the art.

The skilled artisan will also realize that conservative amino acid substitutions may be made in isoprene synthase polypeptides to provide functionally equivalent variants of the foregoing polypeptides, i.e., the variants retain the functional capabilities of the isoprene synthase polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the isoprene synthase polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will not be replaced, or alternatively, will be replaced by conservative amino acid substitutions. Preferably, 1, 2, 3, 4, 5, 6, 7, 8, 9, 10 and so on are changed when preparing variant polypeptides. It is generally preferred that the fewest number of substitutions is made. Thus, one method for generating variant polypeptides is to substitute all other amino acids for a particular single amino acid, then assay activity of the variant, then repeat the process with one or more of the polypeptides having the best activity.

Conservative amino-acid substitutions in the amino acid sequence of isoprene synthase polypeptides to produce functionally equivalent variants of isoprene synthase polypeptides typically are made by alteration of a nucleic acid encoding an isoprene synthase polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding an isoprene synthase polypeptide. In some embodiments, the substitutions can be made by directly synthesizing the peptide. The activity of functionally equivalent fragments of isoprene synthase polypeptides can be tested by cloning the gene encoding the altered isoprene synthase polypeptide into an appropriate expression vector, introducing the vector into an appropriate host cell, expressing the altered isoprene synthase polypeptide, and testing for a functional capability of the isoprene synthase polypeptides as disclosed herein. Peptides which are chemically synthesized can be tested directly for function, e.g., for isoprene synthase function.

Aspects of the invention incorporate optimization strategies that are aimed at increasing production of isoprene from a genetically engineered photosynthetic microorganism. As used herein, increased production of isoprene refers to a higher amount of isoprene being produced from a genetically engineered photosynthetic microorganism after one or more optimization strategies, relative to the amount of isoprene that is produced from a genetically engineered photosynthetic microorganism prior to one or more optimization strategies.

In some embodiments isoprene production in cyanobacteria will be increased by alteration of the expression level of isoprene synthase and through exerting control over the expression of isoprene synthase. A number of promoters and ribosome binding sites that have already been shown to work in cyanobacteria will be tried, for example the (relatively strong in *E. coli*) tacII promoter, and the (relatively weak in *E. coli*) lac promoter, together with associated ribosome binding sites and lac operator sequences (de Boer et al., 1983; Siebenlist et al., 1980). In the absence of co-expressed lac repressor, these two promoters should give two different levels of constitutive expression of the enzyme, which can be quantitated and compared with respect to the level of product (isoprene) produced and performance in the bioreactor. Addition to the construct of a co-expressable lac$^q$ repressor gene under control of a constitutive promoter will allow regulation of expression levels by the concentration in the medium of the non-metabolizable inducer, isopropyl β-D-thiogalactoside (IPTG). This will enable variable levels of isoprene synthase expression to be explored with respect to their effect on productivity and bioreactor performance. This will also allow a decision to be made regarding whether regulatable expression of isoprene synthase is desired or dispensable. If it is dispensable, then once the optimal level of expression is determined, a "hard wired" constitutive expression construct that emulated that level could be created empirically by varying the promoter sequence, the ribosome binding site sequence, the spacing between the ribosome binding site and the start codon, etc. until the expression was tuned to the right level. Note that experiments involving $lac^q$ would have to be conducted at a temperature where the lac repressor was folded and active. Wild type lac repressor is stable up to 50° C. and, if necessary, thermostable mutants of lac repressor (Bell et al., 2001; Gerk et al., 2000) could also be employed.

Transcription termination is a further step in gene expression that could be modified for optimization of isoprene synthase expression. Sequences coding for stem-loop structures, having the properties of potential transcription terminators, have also been found following the stop codons of some cyanobacterial genes, including those from species of *Anabaena* and *Synechococcus* (Li and Tabita, 1994; Plansangkate et al, 2004).

In another embodiment, optimization of expression in cyanobacteria refers to optimization of translation initiation in cyanobacteria. Cyanobacteria are gram negative organisms and tend to have translation initiation sites similar to those found in *E. coli*. Cyanobacterial mRNAs are often found with purine-rich ribosome binding sites (Shine-Dalgarno sequences) several nucleotides upstream of canonical start codons. For example, for the ferredoxin gene in *Anacystis nidulans* R2 a GAGGA is found 7 nucleotides upstream of the methionine start codon (Reith et al., 1986). And in the flavodoxin message of *A. nidulans* a GGAAG is found 9 nucleotides upstream of the AUG start codon (Laudenbach et al., 1988). Other examples can be found in the genome sequences of cyanobacteria in Genbank (www.ncbi.nlm.nih.gov).

In some embodiments isoprene production in cyanobacteria will be increased through protein engineering of the isoprene synthase enzyme. A 3D homology model of the isoprene synthase enzyme can be built by comparison with experimentally determined 3D structures of homologous terpene cyclases such as 5-epi-aristolochene synthase and bornyl diphosphate synthase (Starks et al., 1997; Whittington et al., 2002). In parallel, efforts to experimentally determine the actual 3D structure of the poplar isoprene synthase by X-ray crystallography or NMR spectroscopy—both with and without bound substrate or substrate analogues—would be initiated. The poplar isoprene synthase enzyme is already fairly thermostable, with an activity temperature optimum of 50° C. (Monson et al., 1992). However, should further temperature stabilization be desirable, structure-guided mutagenesis could be employed; for example, substitution of alanines for glycines in alpha helices typically contributes >1 kcal/mol of stabilization free energy per mutation. If further stabilization is required, a strategy of combinatorial mutagenesis involving in vitro evolution will be employed (Martin et al., 2001; Max et al., 2007). To improve the specific activity and specificity of the isoprene synthase a 3D model (or experimental structure—see above) of the enzyme with bound substrate will be generated. A model of the enzyme bound to the transition state complex would also be useful. Based on these models, a series of site-specific amino acid substitution mutations in residues in the region of the active site that are predicted to interact with the substrate or transition state will be generated, and the $k_{cat}$ and $K_m$ values for these variants measured and compared to the respective wild type values. Based on these results, further single site mutations will be generated, as well as all possible combinations of the best single site mutations (Banta et al., 2002), and tested. Improved mutants emerging from this screen will be tested for their enhancement of isoprene production in the recombinant cyanobacterial host under bioreactor culturing conditions. These in vivo tests will also uncover any specificity changes in the engineered enzyme that are deleterious to the host organism.

In some embodiments, isoprene production in cyanobacteria will be increased through over-expression and/or intrinsic activity (Kcat/Km) enhancement of enzymes upstream of isoprenyl diphosphate or dimethylallyl diphosphate synthesis that are limiting. The substrates for isoprene synthase, IPP and DMAPP, are known to be generated by the 2-C-methyl-D-erythritol-4-phosphate pathway in cyanobacteria (Okada and Hase, 2005). Many of the enzymatic steps in this pathway are known, and the components can be cloned and over-expressed (Miller et al, 2001; Hoeffler et al, 2002; Hunter et al, 2003; Okada and Hase, 2005).

In principle, the flux of carbon through this pathway in the recombinant host organism can be increased by identifying the step that is rate-limiting, then over-expressing or engineering for increased specific activity (see above) the enzyme (and co-factor, if necessary) involved in this particular step. For example, isoprene production in *E. coli* was shown to be enhanced by over-expressing a 1-deoxyxylulose 5-phosphate synthase gene, which is "upstream" of dimethylallyl diphosphate synthesis in the *S. leopoliensis* (Miller et al., 2000; Miller et al., 2001). Similarly, one can increase isopentenyl diphosphate isomerase activity in the cell, either by over-expression or engineering a more active enzyme, and thereby promote facile equilibration and balancing of the isopentenyl diphosphate and dimethylallyl diphosphate pools in the cell (Barkley et al, 2004), or over-express inorganic pyrophosphatase in order to "pull" the process by breaking down inorganic pyrophosphate which, along with isoprene, is a product of the isoprene synthase-catalyzed reaction.

This is an iterative process since, generally, when one bottleneck is removed and the metabolic rate through a pathway increases, a new rate-limiting step manifests itself elsewhere in the pathway. Changes in metabolic carbon fluxes resulting from each new modification of the isoprene-producing cyanobacterial organism can be evaluated by culturing the cells in the presence of $^{13}CO_2$ and quantitatively monitoring the levels of carbon-containing metabolites via analyses of the cellular contents by two-dimensional nuclear magnetic resonance spectroscopy (Emmerling et al, 2002). Relief of a new bottleneck can then be pursued by means similar to those used to address the first bottleneck, e.g., over-expression of components and/or protein engineering to increase their specific activity. And any subsequent bottlenecks can be attacked in a similar fashion, until the carbon flux through the pathway reaches a maximum limited by extrinsic factors (e.g., diffusion-controlled mass transfer of $CO_2$ into the cell, light availability, etc.). Note that over-expression of selected genes in the transformed host cyanobacterial organism could be achieved by a number of means: cloning of the gene(s) on multicopy plasmids, insertion of an additional copy or copies of the genes via integration into the host chromosome(s), insertion of cis-acting control elements (e.g., promoters)

adjacent to the genes naturally present in the host chromosome(s) in order to up-regulate them, and other similar strategies.

In some embodiments, isoprene production in cyanobacteria will be increased through random mutagenesis (with transposon or transposon-like insertions or with standard mutagens) and screening for improved organism production. Production of isoprene may also be limited under some circumstances by suppression of certain metabolic pathways in the host organism by endogenous host factors. In these cases, "knocking-out" or down-regulating host factors or sequences that are acting as suppressors would be expected to increase carbon flow through pathways leading to isoprene. Where such suppressors are known, creating a null mutant using gene-disruption via insertion of an antibiotic resistance cassette through a double recombination event is straightforward (Iwai et al., 2004). If a total knock-out of gene activity is undesired due to, e.g., lethality, then "knock-downs" of suppressor activity can be pursued by inserting adjacent cis-acting control elements that allow the gene to be down-regulated. In many cases, however, the identity of genes in the host organism that suppress productivity will not be immediately apparent, but it will nevertheless be possible to modify the activity of such genes via random mutagenesis and screening. The key to such an activity, in which after saturation mutagenesis with a chemical mutagen one might wish to screen tens of thousands of bacterial colonies, is a scaled-down and highly parallelizable assay. Suitable mutagens for performing random mutagenesis are nitrosoguanidine and UV light. Random mutagenesis via transposon insertion could also be performed (Tolonen et al., 2006; Zhang et al., 2004). Mutagenized colonies are picked into the wells of a 96 well (or 48 or 24 well) deep-well microtiter plates containing a small amount of suitable medium, the plates are covered with a gas-permeable membrane, and the plates are incubated with shaking under illumination until the cells reach saturation. Then, after isoprene synthase induction (if necessary), the plates are sealed with a gas-impermeable membrane and the incubation continued, allowing the gaseous isoprene evolved from each microculture to accumulate in the head space above the culture. An autosampler interfaced with a gas chromatography/mass spectrometry instrument could then collect and quantitate the isoprene from each microculture. Mutant clone microcultures exhibiting increased isoprene production, after clonal purification by re-streaking, would be checked for reproducibility of the improved isoprene production phenotype at the shake-flask and bioreactor (3-10 L) scales. For the case of chemical mutagenesis, verified higher-producing strains will be subjected to complete genome re-sequencing and this sequence compared with that of the wild type genome to identify the sites of mutagenesis. In cases where there a multiple sites of mutagenesis observed in a single strain, these may be characterized singly (i.e., against the wild type genetic background) by creating each mutagenized gene in vitro and introducing it into the wild type chromosome(s) via "knock-in" technology. For the case of transposon mutagenesis, mutagenized loci in the genome can be identified and isolated for sequencing using "reverse PCR".

In some embodiments, isoprene production in cyanobacteria will be increased through shotgun cloning of genome fragments from the same or related organisms, followed by screening for improved organism productivity, to identify cryptic pathways that can be added or enhanced by over-expressing factors in trans. Limiting factors that act in trans to stimulate isoprene production can be supplied (and identified) by shotgun cloning into the isoprene-producing organism genomic sequences, either from the same organism (in cases where increased gene copy number is desired), or from other organisms such as other bacterial (especially cyanobacterial) species where related but potentially more efficacious genes may be present. The only requirement is that the genomic sequences must be supplied in a context that enables their expression in the host organism, which can be satisfied in many cases by the endogenous control sequences (e.g., promoters) or, if necessary, by expression control sequences supplied on the cloning vector. Screening of clones for increased isoprene production will be carried out in a similar fashion and using the same microtiter plate assay as described above for screening randomly mutagenized clones. Clones with verified increases in isoprene production at the shake flask and bioreactor scale can be characterized by DNA sequencing after using the flanking vector sequences to amplify via PCR the inserted genome fragments.

In some embodiments, isoprene production in cyanobacteria will be increased through combining mutations in a single organism. Once two or more new mutations, new gene insertions, or other genetic modifications are shown to reproducibly enhance the productivity of the organism, then all possible combinations of these modifications will be tested. Assuming that the actual genetic modification in each case has been characterized via DNA sequencing, using standard molecular genetic manipulations it will be possible to engineer, in a combinatorial fashion, multiple independent "up" mutations into a single genome. Each such doubly-mutated, triply-mutated, etc. organism can then be tested for additivity, synergism, or antagonism of each individual genetic modification in the context of each of the others. By using genetic modifications that exhibit additivity or synergy as building blocks and combining these it will be possible to create isoprene-producing organisms with further enhancements in productivity.

Aspects of the invention relate to culturing cyanobacteria. All characterized species of cyanobacteria have been successfully cultured on at least the laboratory scale. Many of these grow on standard medium for "blue green algae" such as BG-11 (ATCC medium 616). Also, many specialized culture media have been developed. Thus, cyanobacteria can be cultured in standard or specialized media, including but not limited to: Aiba and Ogawa (AO) Medium, Allen and Arnon Medium plus Nitrate: ATCC Medium 1142, Antia's (ANT) Medium, Aquil Medium, Ashbey's Nitrogen-free Agar, ASN-III Medium, ASP 2 Medium, ASW Medium: Artificial Seawater and derivatives, ATCC Medium 617: BG-11 for Marine Blue-Green Algae; Modified ATCC Medium 616 [BG-11 medium], ATCC Medium 819: Blue-green Nitrogen-fixing Medium; ATCC Medium 616 [BG-11 medium] without NO3, ATCC Medium 854: ATCC Medium 616 [BG-11 medium] with Vitamin B12, ATCC Medium 1047: ATCC Medium 957 [MN marine medium] with Vitamin B12, ATCC Medium 1077: Nitrogen-fixing marine medium; ATCC Medium 957 [MN marine medium] without NO3, ATCC Medium 1234: BG-11 Uracil medium; ATCC Medium 616 [BG-11 medium] with uracil, Beggiatoa Medium: ATCC Medium 138, Beggiatoa Medium 2: ATCC Medium 1193, BG-11 Medium for Blue Green Algae: ATCC Medium 616, Blue-Green (BG) Medium, Bold's Basal (BB) Medium, Castenholtz D Medium, Castenholtz D Medium Modified: Halophilic cyanobacteria, Castenholtz DG Medium, Castenholtz DGN Medium, Castenholtz ND Medium, Chloroflexus Broth, Chloroflexus Medium: ATCC Medium 920, Chu's #10 Medium: ATCC Medium 341, Chu's #10 Medium Modified, Chu's #11 Medium Modified, DCM Medium, DYIV Medium, E27 Medium, E31 Medium and Derivatives, f/2

Medium, f/2 Medium Derivatives, Fraquil Medium: Freshwater Trace Metal-Buffered Medium, Gorham's Medium for Algae: ATCC Medium 625, h/2 Medium, Jaworski's (JM) Medium, K Medium, L1 Medium and Derivatives, MN Marine Medium: ATCC Medium 957, Plymouth Erdschreiber (PE) Medium, Prochlorococcus PC Medium, Proteose Peptone (PP) Medium, Prov Medium, Prov Medium Derivatives, S77 plus Vitamins Medium, S88 plus Vitamins Medium, Saltwater Nutrient Agar (SNA) Medium and Derivatives, SES Medium, SN Medium, Modified SN Medium, SNAX Medium, Soil/Water Biphasic (S/W) Medium and Derivatives, SOT Medium for Spirulina: ATCC Medium 1679, Spirulina (SP) Medium, van Rijn and Cohen (RC) Medium, Walsby's Medium, Yopp Medium, Z8 Medium (http://www-cyanosite.bio.purdue.edu/media/table/media.html and (Castenholz, 1998)). Culturing of cyanobacteria is conducted according to standard methods, which are known to those of skill in the art (Rogers and Gallon, 1988; Burlew, 1961; Round, 1965). These conditions include sufficient light, since the microorganisms are genetically engineered photosynthetic microorganisms.

In some embodiments isoprene production in cyanobacteria will be increased through improvement of culturing protocols in a cyanobacterial bioreactor. Standardized protocols that give reproducible isoprene production for a given strain and a given set of conditions are critical. In general, for each new strain archival vial lots will be created, numbered and dated, and stored at −80° C. or in liquid nitrogen. For reproducibility, each new experimental culture with that strain will be initiated by thawing a new vial lot and using it to seed the culture. Standard culture media and conditions (e.g., Burlew, 1961) will be taken as the starting point for culture optimization. Culture conditions will be explored in order to establish the optimal protocol for growth of the recombinant organism prior to the production phase. Some culture conditions to be independently varied and optimized for a given bioreactor configuration include: wavelength vs. intensity spectrum of the illuminating light; pH; temperature; trace metals; media supplementation with complex nitrogen sources (e.g., yeast extract); dissolved $CO_2$ concentration (see Frick and Junker, 1999, for a discussion of issues related to dissolved $CO_2$ in fermentation broths); dissolved $O_2$ concentration; dissolved $N_2$ concentration; impeller design and rate of agitation (note: includes agitation by air lift mechanisms); presence of antifoaming agents; presence of organic co-solvents (Daugulis, 2001); final optical density under conditions of nutrient limitation; etc. Optimization may also include varying any or all of these variables as a function of time or of the optical density of the culture. An additional optimization may need to be performed during the production phase in order to maximize output of isoprene. This is especially true in the case of inducible expression systems for the isoprene synthase and/or other genes in the metabolic pathways synthesizing isoprene synthase substrates, where the optimal post-induction (production phase) cell culturing protocols may differ in significant ways from the optimum pre-induction (growth phase) protocols. Also note that every time a new recombinant strain is tested, or the scale or the geometry of the bioreactor is altered, all protocols may need to be re-optimized.

Aspects of the invention relate to collecting isoprene from a metabolically engineered photosynthetic microorganism. The photosynthetic organism could be cultured in a fermentor. In a bacterial culture above 34° C., the isoprene is gaseous. Thus, the isoprene can be collected in the off-gas of the fermentation through simple condensation.

In some embodiments, isoprene production in cyanobacteria will be increased through improvement of harvesting protocols. Volatile organic compounds produced by bacterial cultures can be harvested from the off-gas of the culture using a chilled condenser apparatus to re-liquefy the gaseous compounds (Miller et al., 2000; Newman et al., 2006). Evaporated water in the off-gas is also trapped by this procedure. If desired, a series of condensers or cold traps can be set up with decreasing temperatures in order to fractionate the condensate into its more and less volatile components (Newman et al., 2006). The design, operating temperature, and number of such condensers can be established empirically. Even without fractionation, however, isoprene can be easily separated from co-condensed water: because it is relatively immiscible and of lower density, a phase separation allows relatively pure isoprene to be harvested from the upper phase of a two-phase condensate. Alternatively, in the bioreactor itself an immiscible organic co-solvent such as n-dodecane could be added to trap the isoprene, if desired, in the non-aqueous phase, from which it could be later separated (Daugulis, 2001; Janikowski et al., 2002; Newman et al., 2006).

The present invention is illustrated by the following examples, which are not intended to be limiting in any way.

EXAMPLES

Example 1

Synthesizing a Gene for Isoprene Synthase (v2.2)

A cDNA clone for isoprene synthase has been cloned from the poplar (Miller et al., 2001). Expression of this foreign gene in *E. coli*, and production of isoprene from the recombinant organism, has also been demonstrated (Miller et al., 2001). The class of enzymes to which isoprene synthase belongs, terpene cyclases, has been relatively well-studied (including determinations of the 3D structures of the homologs 5-epi-aristolochene synthase (Starks et al., 1997) and bornyl diphosphate synthase (Whittington et al., 2002)), which should greatly aid future protein engineering experiments aimed at optimizing the enzyme.

A gene encoding isoprene synthase is synthesized using the poplar sequence as a guide, but modifying the sequence to (a) provide optimized codons for expression in *T. elongatus*, (b) remove or insert certain restriction sites (e.g., sites recognized by the *T. elongatus* restriction enzyme system (Iwai et al., 2004) or sites necessary for molecular biological manipulations), and/or mutate the amino acid sequence to favorably alter the physical properties of the isoprene synthase protein itself (e.g, provide more thermostability, etc.).

Example 2

Engineering *Thermosynechococcus elongatus* BP-1 to Express Isoprene Synthase

*Thermosynechococcus elongatus* BP-1 is a particularly favorable cyanobacteria strain with which to assess expression of isoprene synthase. There has been extensive characterization of the photosynthetic machinery of this microorganism (Rutherford and Boussac, 2004) and the complete DNA sequence of its genome has been determined and annotated (Nakamura et al., 2002). Moreover, transformation with plasmids via electroporation and expression of foreign genes has been demonstrated (Iwai et al., 2004). Thus, all the basic tools exist for metabolic engineering with *T. elongatus*. As a final advantage, *T. elongatus* has an optimal growth temperature of 55° C., more than 20° above the boiling point for isoprene, meaning that the kinetics of isoprene volatilization from the living cells should be extremely favorable, "pulling" the reaction forward.

The synthetic isoprene synthase gene is inserted into a vector behind a promoter that is transcriptionally active in *T. elongatus*; such vector can also contain markers allowing for selection of positive transformants in *T. elongatus* (Iwai et al., 2004).

Example 3

Test Cultures

Test cultures of the recombinant strain on minimal medium containing trace elements but no carbon source (apart from $CO_2$) are conducted to establish photosynthetic production of isoprene from carbon dioxide, according to three criteria: (i) detection of levels of off-gassed isoprene significantly higher than those found in the off-gas from non-recombinant control cells; (ii) demonstration of the light-inducibility and light-dependence of isoprene synthesis; and (iii) demonstration that the isoprene can be isotopically labeled by culturing the recombinant organism in the presence of $^{13}CO_2$.

Example 4

Synthesizing and Expressing a Gene for Isoprene Synthase (v2.2.1) in Cyanobacteria and Detection of Culture-Derived Isoprene Briefly, a synthetic isoprene synthase gene, cloned into the vector pUC57 as a PstI/KpnI fragment (FIG. 6), was constructed. Selected alterations of the poplar enzyme coding sequence to remove certain restriction enzyme sites and to substitute rare codons (based on *T. elongatus* BP-1 codon usage) for more common ones, as well as several other base changes, are indicated by underlining. The start (ATG) and stop (TAA) codons are indicated in bold.

To facilitate detection and/or purification of the recombinant enzyme a $His_6$ tag coding sequence has been fused 5' to the enzyme coding sequence immediately after the start codon. This tag should facilitate detection of the recombinant enzyme in situ on SDS gels using InVision™ stain (Invitrogen, Inc.) and/or purification of the recombinant enzyme from cell extracts using immobilized metal affinity chromatography. Immediately upstream of the start codon is a ribosome binding site sequence preceded by a tacII promoter (de Boer et al, 1983); a unique EcoRI site between the start codon and the ribosome binding site allows the fragment containing these upstream control sequences to be separated from the coding sequences, if desired. This coding sequence, with or without further "tailoring" of the ends, was placed under control of the *Anabaena* pNir promoter which drives expression of the gene encoding nitrate reductase (Desplancq, D. et al, 2005).

Desplancq et al, includes the construction of p505 with the pNir promoter driving the transcription of the hetR gene. We cut out the hetr gene with EcoRI and BamHI and replaced it with the amplified isoprene synthase gene. The primers used to amplify the isoprene synthesas gene with the EcoRI and BamHI sites attached were the following:

```
                                            [SEQ ID NO: 2]
EccoRI-    5'-CAGGAATTCATGGCAACTGAATTATTGTGCTTG-3'

[SEQ ID NO: 3]
BamHI-     5'-CAAGGATCCTTATCGCTCAAAGGGTAGAA-3'.
```

This promoter is OFF in cells growing on ammonia as nitrogen source but ON strongly in cells growing on nitrate. For engineering applications this promoter is useful for short-term batch applications, but not generally applicable because the nitrate is consumed during growth.

This construct was maintained as a plasmid in *Anabaena* 7120 by continuous selection in neomycin at 25 C. After 10 days visible colonies were picked and transferred to liquid medium, either BG-11 or BG-11 without combined nitrogen, but with neomycin. After ten days of growth, nitrate was added to the $BG-11_0$ culture to induce transcription of isoprene synthase. The isoprene synthase transcript was detected by RT-PCR. After several days the cell culture temperature was increased to 37 C to permit conversion of any isoprene produced to the gas phase.

Test fermentations of the transformed strains on minimal medium containing trace elements but no carbon source (apart from $CO_2$) were conducted to establish photosynthetic production of isoprene from carbon dioxide. Successful expression of the isoprene synthase gene in the recombinant cyanobacteria was demonstrated by the following outcomes:

(a) Transformed cells by comparison with appropriate control strains were demonstrated to have the ability to transcribe IS mRNA by PCR.

(b) Biosynthetic production of isoprene from recombinant cell cultures was demonstrated by gas chromatography/mass spectrometry using protocols developed to detect isoprene given off by bacterial cultures (Kuzma et al, 1995—see below). Levels of outgassed isoprene were higher than those found in the outgas from non-recombinant control cells. The calculated yield of isoprene under the conditions listed are 25 micrograms per liter per 30 min of a culture at OD700=0.23.

The isoprene product was harvested by passing the off-gas through a condenser and then washing it out of the condenser with the solvent dichloroethane. The (concentrated) DCE solution is injected into the GC for quantitation.

Assays of Isoprene Produced by Bacterial Cell Cultures (from Kuzma et al., 1995).

Identification of Isoprene by Gas Chromatography-Mass Spectrometry (GC-MS).

Bacteria are inoculated into 10 ml of rich media and grown to an $A_{600}$ of approximately 1.5. Then, 2 ml of culture are incubated in 4.8 ml glass vials sealed with Teflon-lined septa for approximately 6 hours. The sample headspace (1.2 ml) is collected in a nickel loop packed with glass beads immersed in liquid argon (−186° C.). The loop is subsequently heated to 150° C. and injected into a DB-1 column (30 m long, 0.25 mm diameter, 1 μm film thickness) (J & W Scientific, Folsom, Calif.) connected to a 5971A Hewlett Packard mass selective detector (electron ionization, operated in total ion mode) or an equivalent instrument. The temperature program for each GC-MS run includes a 1 minute hold at −65° C. followed by a warming rate of 4° C. per minute. Helium carrier gas and a flow rate of approximately 0.7 ml $min^{-1}$ are used. This system is described in more detail in Cicerone et al. (1988). For the positive identification of bacterial isoprene production, peak retention times and mass spectra obtained from bacterial headspace are compared with the retention time and mass spectrum of an authentic isoprene standard. The headspace from a "vector only" recombinant control culture should be run as a negative control.

Routine Isoprene Assays.

Bacterial strains are grown to an $A_{600}$ ranging from 1.0 to 6.0. Two ml of culture are incubated in sealed vials at an appropriate temperature with shaking for approximately 3 hours; headspace is analyzed with a gas chromatography (GC) system that is highly sensitive to isoprene (for example, see Greenberg et al., 1993, and Silver and Fall, 1991). The system is operated isothermally (85° C.) with an n-octane/ porasil C column (Alltech Associates, Inc., Deerfield, Ill.) and is coupled to an RGD2 mercuric oxide reduction gas detector (Trace Analytical, Menlo Park, Calif.) or its equivalent. Isoprene elutes at 3.6 minutes. Isoprene production rates (nmol $g^{-1}$ $h^{-1}$) can be calculated as follows: GC area units are converted to nmol isoprene via a standard isoprene concentration calibration curve; $A_{600}$ values for the samples are taken and converted to grams of cells (g) by obtaining wet weights for cell cultures with a known $A_{600}$. Two to five separate measurements are taken and averaged for each assay point. Negative controls are as above.

REFERENCES

Arundale, E. and Mikeska, L. A. (1952). The Olefin-Aldehyde Condensation. The Prins Reaction. Chemical Reviews 51, 505-555.

Banta, S., Swanson, B. A., Wu, S., Jarnagin, A., and Anderson, S. (2002). Optimizing an artificial metabolic pathway: engineering the cofactor specificity of Corynebacterium 2,5-diketo-D-gluconic acid reductase for use in vitamin C biosynthesis. Biochemistry 41, 6226-6236.

Barkley, S. J., Desai, S. B., and Poulter, C. D. (2004). Type II isopentenyl diphosphate isomerase from Synechocystis sp. strain PCC 6803. J. Bacteriol. 186, 8156-8158.

Bell, C. E., Barry, J., Matthews, K. S., and Lewis, M. (2001). Structure of a variant of lac repressor with increased thermostability and decreased affinity for operator. J. Mol. Biol. 313, 99-109.

Bickle, T. A. and Kruger, D. H. (1993). Biology of DNA restriction. Microbiol. Rev. 57, 434-450.

Billi, D., Friedmann, E. I., Helm, R. F., and Potts, M. (2001). Gene transfer to the desiccation-tolerant cyanobacterium Chroococcidiopsis. J. Bacteriol. 183, 2298-2305.

Bruns, B. U., Briggs, W. R., and Grossman, A. R. (1989). Molecular characterization of phycobilisome regulatory mutants of Fremyella diplosiphon. J. Bacteriol. 171, 901-908.

Burlew, J. S., Algal Culture: From Laboratory to Pilot Plant, Carnegie Institution of Washington, Publication 600, Washington, D.C., 1961;

Castenholz, R. W. (1998). Culturing methods for cyanobacteria. Methods Enzymol. 167, 68-93.

Castenholz, R. W. 2001. Phylum B X. Cyanobacteria. Oxygenic Photosynthetic Bacteria. In: Bergey's Manual of Systematic Bacteriology. Volume 1: The Archaea and the Deeply Branching and Phototropic Bacteria. Second Edition. G. Garrity, D. R. Boone, and R. W. Castenholz (eds.) Springer-Verlag, New York.

Cicerone, R. J., Heidt, L. E., and Pollock, W. H. (1988). Measurements of atmospheric methyl bromide and bromoform. J. Geophys. Res. 93, 3745-3749.

Cunningham, F. X., Jr., Lafond, T. P., and Gantt, E. (2000). Evidence of a role for LytB in the nonmevalonate pathway of isoprenoid biosynthesis. J. Bacteriol. 182, 5841-5848.

Daugulis, A. J. (2001). Two-phase partitioning bioreactors: a new technology platform for destroying xenobiotics. Trends Biotechnol. 19, 457-462.

de Boer, H. A., Comstock, L. J., and Vasser, M. (1983). The tac promoter: a functional hybrid derived from the trp and lac promoters. Proc. Natl. Acad. Sci. U.S.A 80, 21-25.

Deng, M. D. and Coleman, J. R. (1999). Ethanol synthesis by genetic engineering in cyanobacteria. Appl. Environ. Microbiol. 65, 523-528.

Desplancq, D. Bernard., C., Sibler, A-P., Kieffer, B., Miguet, L., Potier, N., Van Dorsselaer, A. and Weiss E. (2005). Combining inducible protein overexpression with NMR-grade triple isotope labeling in the cyanobacterium Anabaena sp. PCC 7120. Biotechniques, 39, 405-411.

Emmerling, M., Dauner, M., Ponti, A., Fiaux, J., Hochuli, M., Szyperski, T., Wüthrich, K., Bailey, J. E., and Sauer, U. (2002). Metabolic flux responses to pyruvate kinase knockout in Escherichia coli. J. Bacteriol. 184, 152-164.

Ershov, Y. V., Gantt, R. R., Cunningham, J. F., Jr., and Gantt, E. (2002). Isoprenoid biosynthesis in Synechocystis sp. strain PCC6803 is stimulated by compounds of the pentose phosphate cycle but not by pyruvate or deoxyxylulose-5-phosphate. J. Bacteriol. 184, 5045-5051.

Farrell, A. E., Plevin, R. J., Turner, B. T., Jones, A. D., O'Hare, M., and Kammen, D. M. (2006). Ethanol can contribute to energy and environmental goals. Science 311, 506-508.

Frick, R. and Junker, B. (1999). Indirect methods for characterization of carbon dioxide levels in fermentation broth. J. Biosci. Bioeng. 87, 344-351.

Gerk, L. P., Leven, O., and Muller-Hill, B. (2000). Strengthening the dimerisation interface of Lac repressor increases its thermostability by 40 deg. C. J. Mol. Biol. 299, 805-812.

Greenberg, J. P., Zimmerman, P. R., Taylor, B. E., Silver, G. M., and Fall, R. (1993). Sub-parts per billion detection of isoprene using a reduction gas detector with a portable gas chromatograph. Atmos. Environ. 27A, 2689-2692.

Grigorieva, G. and Shestakov, S. (1982). Transformation in the Cyanobacterium Synechocystis Sp 6803. Ferns Microbiology Letters 13, 367-370.

Hahn-Hagerdal, B., Galbe, M., Gorwa-Grauslund, M. F., Eiden, G., and Zacchi, G. (2006). Bio-ethanol—the fuel of tomorrow from the residues of today. Trends Biotechnol. 24, 549-556.

Hoeffler, J. F., Tritsch, D., Grosdemange-Billiard, C., and Rohmer, M. (2002). Isoprenoid biosynthesis via the methylerythritol phosphate pathway. Mechanistic investigations of the 1-deoxy-D-xylulose 5-phosphate reductoisomerase. Eur. J. Biochem. 269. 4446-4457.

Hunter, W. N., Bond, C. S., Gabrielsen, M., and Kemp, L. E. (2003). Structure and reactivity in the non-mevalonate pathway of isoprenoid biosynthesis. Biochem. Soc. Trans. 31, 537-542.

Iwai, M., Katoh, H., Katayama, M., and Ikeuchi, M. (2004). Improved genetic transformation of the thermophilic cyanobacterium, Thermosynechococcus elongatus BP-1. Plant Cell Physiol. 45, 171-175.

Janikowski, T. B., Velicogna, D., Punt, M., and Daugulis, A. J. (2002). Use of a two-phase partitioning bioreactor for degrading polycyclic aromatic hydrocarbons by a Sphingomonas sp. Appl. Microbiol. Biotechnol. 59, 368-376.

Kawata, Y., Yano, S., Kojima, H., and Toyomizu, M. (2004). Transformation of Spirulina platensis strain C1 (Arthrospira sp. PCC9438) with Tn5 transposase-transposon DNA-cation liposome complex. Mar. Biotechnol. (NY) 6, 355-363.

Koksharova, O. A. and Wolk, C. P. (2002). Genetic tools for cyanobacteria. Appl. Microbiol. Biotechnol. 58, 123-137.

Kuzma. J., Nemecek-Marshall, M., Pollock, W. H., and Fall, R. (1995). Bacteria produce the volatile hydrocarbon isoprene. Curr. Microbiol. 30, 97-103.

Laudenbach, D. E., Reith, M. E., and Straus, N. A. (1988). Isolation, sequence analysis, and transcriptional studies of the flavodoxin gene from Anacystis nidulans R2. J. Bacteriol. 170, 258-265.

Larsson, S., Quintana-Sainz, A., Reimann, A., Nilvebrant, N. O., and Jonsson, L. J. (2000). Influence of lignocellulose-derived aromatic compounds on oxygen-limited growth and ethanolic fermentation by Saccharomyces cerevisiae. Appl. Biochem. Biotechnol. 84-86, 617-632.

Li, L.-A., and Tabita, R. (1994) Transcription control of ribulose bisphosphate carboxylase/oxygenase activase and adjacent genes in *Anabaena* species. J. Bacteriol. 176, 6697-6706.

Marraccini, P., Cassier-Chauvat, C., Bulteau, S., Chavez, S., and Chauvat, F. (1994). Light-regulated promoters from *Synechocystis* PCC6803 share a consensus motif involved in photoregulation. Mol. Microbiol. 12, 1005-1012.

Martin, A., Sieber, V., and Schmid, F. X. (2001). In-vitro selection of highly stabilized protein variants with optimized surface. J. Mol. Biol. 309, 717-726.

Max, K. E., Wunderlich, M., Roske, Y., Schmid, F. X., and Heinemann, U. (2007). Optimized variants of the cold shock protein from in vitro selection: structural basis of their high thermostability. J. Mol. Biol. 369, 1087-1097.

Mermet-Bouvier, P., Cassier-Chauvet, C., Marraccini, P., and Chauvat, F. (1993). Transfer and Replication of RSF1010-Derived Plasmids in Several Cyanobacteria of the Genera *Synechocystis* and *Synechococcus*. Curr. Microbiol. 27, 323-327.

Miller, S. R. and Castenholz, R. W. (2000). Evolution of thermotolerance in hot spring cyanobacteria of the genus *Synechococcus*. Appl. Environ. Microbiol. 66, 4222-4229.

Miller, B., Heuser, T., and Zimmer, W. (2000). Functional involvement of a deoxy-D-xylulose 5-phosphate reductoisomerase gene harboring locus of *Synechococcus leopoliensis* in isoprenoid biosynthesis. FEBS Letters 481, 221-226.

Miller, B., Oschinski, C., and Zimmer, W. (2001). First isolation of an isoprene synthase gene from poplar and successful expression of the gene in *Escherichia coli*. Planta 213, 483-487.

Miyake, M., Kotani, H., and Asada, Y. (1992). Isolation and identification of restriction endonuclease, SeII from a cyanobacterium, *Synechococcus elongatus*. Nucleic Acids Res. 20, 2605.

Monson, R. K., Jaeger, C. H., Adams, W. W., Driggers, E. M., Silver, G. M., and Fall, R. (1992). Relationships among Isoprene Emission Rate, Photosynthesis, and Isoprene Synthase Activity as Influenced by Temperature. Plant Physiol. 98, 1175-1180.

Moser, D. P., Zarka, D., and Kailas, T. (1993). Characterization of a restriction barrier and electrotransformation of the cyanobacterium Nostoc PCC 7121. Arch. Microbiol. 160, 229-237.

Mosier, N., Wyman, C., Dale, B., Elander, R., Lee, Y. Y., Holtzapple, M., and Ladisch, M. (2005). Features of promising technologies for pretreatment of lignocellulosic biomass. Bioresour. Technol. 96, 673-686.

Muhlenhoff, U. and Chauvat, F. (1996). Gene transfer and manipulation in the thermophilic cyanobacterium *Synechococcus elongatus*. Mol. Gen. Genet. 252, 93-100.

Murray, N.E. (2000). Type I restriction systems: sophisticated molecular machines (a legacy of Bertani and Weigle). Microbiol. Mol. Biol. Rev. 64, 412-434.

Nakamura, Y., Kaneko, T., Sato, S., Ikeuchi, M., Katoh, H., Sasamoto, S., Watanabe, A., Iriguchi, M., Kawashima, K., Kimura, T., Kishida, Y., Kiyokawa, C., Kohara, M., Matsumoto, M., Matsuno, A., Nakazaki, N., Shimpo, S., Sugimoto, M., Takeuchi, C., Yamada, M., and Tabata, S. (2002). Complete genome structure of the thermophilic cyanobacterium *Thermosynechococcus elongatus* BP-1. DNA Res. 9, 123-130.

Newman, J. D., Marshall, J., Chang, M., Nowroozi, F., Paradise, E., Pitera, D., Newman, K. L., and Keasling, J. D. (2006). High-level production of amorpha-4,11-diene in a two-phase partitioning bioreactor of metabolically engineered *Escherichia coli*. Biotechnol. Bioeng. 95, 684-691.

Niebylski, L. M. Fuel Compositions for Reducing Combustion Chamber Deposits and Hydrocarbon Emissions of Internal Combustion Engines. [U.S. Pat. No. 4,191,436]. 1980. Ref Type: Patent Okada, K. and Hase, T. (2005). Cyanobacterial non-mevalonate pathway: (E)-4-hydroxy-3-methylbut-2-enyl diphosphate synthase interacts with ferredoxin in *Thermosynechococcus elongatus* BP-1. J. Biol. Chem. 280, 20672-20679.

Onai, K., Morishita, M., Kaneko, T., Tabata, S., and Ishiura, M. (2004). Natural transformation of the thermophilic cyanobacterium *Thermosynechococcus elongatus* BP-1: a simple and efficient method for gene transfer. Mol. Genet. Genomics 271, 50-59.

Oren, A. (2004). A proposal for further integration of the cyanobacteria under the Bacteriological Code. Int. J. Syst. Evol. Microbiol. 54, 1895-1902.

Plansangkate, P., Fa-aroonswawat, S., Panyim, S., and Chungjatupornchai, W. (2004) The light-responsive promoter of cyanobacterial ORF76 gene overlaps with the htpG terminator. FEMS Microbiol. 235, 341-347.

Price, G. D. and Badger, M. R. (1989). Expression of Human Carbonic Anhydrase in the Cyanobacterium *Synechococcus* PCC7942 Creates a High CO(2)-Requiring Phenotype: Evidence for a Central Role for Carboxysomes in the CO(2) Concentrating Mechanism. Plant Physiol. 91, 505-513.

Ravindran, C. R., Suguna, S., and Shanmugasundaram, S. (2006). Electroporation as a tool to transfer the plasmid pRL489 in *Oscillatoria* MKU 277. J. Microbiol. Methods 66, 174-176.

Reith, M. E., Laudenbach, D. E., and Straus, N. A. (1986). Isolation and nucleotide sequence analysis of the ferredoxin 1 gene from the cyanobacterium *Anacystis nidulans* R2. J. Bacteriol. 168, 1319-1324.

Rippka, R., Deruelles, J., Waterbury, J. B., Herdman, M., and Stanier, R. Y. (1979). Generic Assignments, Strain Histories and Properties of Pure Cultures of Cyanobacteria. Journal of General Microbiology 111, 1-61.

Rogers, L. J., and Gallon, J. R., *Biochemistry of the Algae and Cyanobacteria*, Clarendon Press, Oxford, 1988;

Round, F. E., *Biology of the Algae*, St. Martin's Press, New York, 1965.

Rutherford, A. W. and Boussac, A. (2004). Photosynthesis, a green chemistry driven by solar energy. Clefs CEA 49, 86-92.

Siebenlist, U., Simpson, R. B., and Gilbert, W. (1980). *E. coli* RNA polymerase interacts homologously with two different promoters. Cell 20, 269-281.

Silver, G. M. and Fall, R. (1991). Enzymatic synthesis of isoprene from dimethylallyl diphosphate in aspen leaf extracts. *Plant Physiol.* 97, 1588-1591.

Sode, K., Tatara, M., Takeyama, H., Burgess, J. G., and Matsunaga, T. (1992). Conjugative Gene-Transfer in Marine Cyanobacteria—*Synechococcus* Sp, *Synechocystis* Sp and *Pseudanabaena* Sp. Applied Microbiology and Biotechnology 37, 369-373.

Söderström, J., Galbe, M., and Zacchi, G. (2005). Separate versus Simultaneous Saccharification and Fermentation of Two-Step Steam Pretreated Softwood for Ethanol Production. J. Wood Chem. Technol. 96, 187-202.

Soltes-Rak, E., Kushner, D. J., Williams, D. D., and Coleman, J. R. (1993). Effect of promoter modification on mosquitocidal cryIVB gene expression in *Synechococcus* sp. strain PCC 7942. Appl. Environ. Microbiol. 59, 2404-2410.

Starks, C. M., Back, K., Chappell, J., and Noel, J. P. (1997). Structural basis for cyclic terpene biosynthesis by tobacco 5-epi-aristolochene synthase, Science 277, 1815-1820.

Szalay, A. A. and Williams, J. G. K. Genetic engineering in cyanobacteria. [4778759]. 1988. Ref Type: Patent.

Tengborg, C., Galbe, M., and Zacchi, G. (2001). Reduced inhibition of enzymatic hydrolysis of steam-pretreated softwood. Enzyme Microb. Technol. 28, 835-844.

Thiel, T. (1994). Genetic analysis of cyanobacteria. In The molecular biology of cyanabacteria, D. A. Bryant, ed. Kluwer Dordrecht), pp. 581-611.

Thiel, T. and Poo, H. (1989). Transformation of a filamentous cyanobacterium by electroporation. J. Bacteriol. 171, 5743-5746.

Tolonen, A. C., Liszt, G. B., and Hess, W. R. (2006). Genetic manipulation of Prochlorococcus strain MIT9313: green fluorescent protein expression from an RSF1010 plasmid and Tn5 transposition. Appl. Environ. Microbiol. 72, 7607-7613.

Tsinoremas N F, Kutach A K, Strayer C A, Golden S S (1994). Efficient gene transfer in *Synechococcus* sp. strains PCC 7942 and PCC 6301 by interspecies conjugation and chromosomal recombination. J Bacteriol. November 176 (21), 6764-8.

Whittington, D. A., Wise, M. L., Urbansky, M., Coates, R. M., Croteau, R. B., and Christianson, D. W. (2002). Bornyl diphosphate synthase: structure and strategy for carbocation manipulation by a terpenoid cyclase. Proc. Natl. Acad. Sci. U.S.A. 99, 15375-14380.

Yamaoka, T., Satoh, K., and Kotoh, S. (1978). Photosynthetic activities of a thermophilic blue-green alga. Plant Cell Physiol. 19, 943-954.

Zhang, S., Laborde, S. M., Erankel, L. K., and Bricker, T. M. (2004). Four novel genes required for optimal photoautotrophic growth of the cyanobacterium *Synechocystis* sp. strain PCC 6803 identified by in vitro transposon mutagenesis. J. Bacteriol. 186, 875-879.

The teachings of all references cited herein are hereby incorporated by reference.

---

SEQUENCE LISTING

```
<160> NUMBER OF SEQ ID NOS: 16

<210> SEQ ID NO 1
<211> LENGTH: 61
<212> TYPE: DNA
<213> ORGANISM: Anacystis nidulans

<400> SEQUENCE: 1
ttgatagcat ttctcgcggc gcagttcgcc ctttggcaac ccatagtatc aatgggaaag    60
g                                                                    61

<210> SEQ ID NO 2
<211> LENGTH: 33
<212> TYPE: DNA
<213> ORGANISM: Artificial Sequence
<220> FEATURE:
<223> OTHER INFORMATION: primer used to amplify the isoprene synthase
      gene

<400> SEQUENCE: 2
caggaattca tggcaactga attattgtgc ttg                                  33

<210> SEQ ID NO 3
<211> LENGTH: 29
<212> TYPE: DNA
<213> ORGANISM: Artificial Sequence
<220> FEATURE:
<223> OTHER INFORMATION: primer used to amplify the isoprene synthase
      gene

<400> SEQUENCE: 3
caaggatcct tatcgctcaa agggtagaa                                       29

<210> SEQ ID NO 4
<211> LENGTH: 2062
<212> TYPE: DNA
<213> ORGANISM: Artificial Sequence
<220> FEATURE:
<223> OTHER INFORMATION: Populus alba x Populus tremula mRNA for
      isoprene synthase (ispS gene)

<400> SEQUENCE: 4
```

```
cgcggccgcg tcgacgagag agagaaaatc ctgctgcagt ttccattact agaggcatgg      60
caactgaatt attgtgcttg caccgtccaa tctcactgac acacaaactg ttcagaaatc     120
ccttacctaa agtcatccag gccactccct taactttgaa actcagatgt tctgtaagca     180
cagaaaacgt cagcttcaca gaaacagaaa cagaagccag acggtctgcc aattatgaac     240
caaatagctg ggattatgat tttttgctgt cttcagacac tgacgaatcg attgaagtat     300
acaaagacaa ggccaaaaag ctggaggctg aggtgagaag agagattaac aatgaaaagg     360
cagagttttt gactctgctt gaactgatag ataatgtcca aaggttagga ttgggttacc     420
ggttcgagag tgacataagg agagccctcg acagatttgt ttcttcagga ggatttgatg     480
gtgttacaaa aactagcctt catgctactg ctcttagctt caggcttctc agacagcatg     540
gctttgaggt ctctcaagaa gcgttcagtg gattcaagga tcaaaatggc aatttcttgg     600
aaaaccttaa ggaggacacc aaggcaatac taagcctata tgaagcttca tttcttgcat     660
tagaaggaga aaatatcttg gatgaggcca gggtgtttgc aatatcacat ctaaaagagc     720
tcagcgaaga aaagattgga aaagagctgg ccgaacaggt gaatcatgca ttggagcttc     780
cattgcatcg caggacgcaa agactagaag ctgtttggag tattgaagca taccgtaaaa     840
aggaagatgc aaatcaagta ctgctagaac ttgctatatt ggactacaac atgattcaat     900
cagtatacca aagagatctt cgcgagacat caaggtggtg gaggcgagtg ggtcttgcaa     960
caaagttgca ttttgctaaa gacaggttaa ttgaaagctt ttactgggca gttggagttg    1020
cgttcgaacc tcaatacagt gattgccgta attcagtagc aaaaatgttt tcatttgtaa    1080
caatcattga tgatatctat gatgtttatg gtactctgga tgagctggag ctatttacag    1140
atgctgttga gagatgggat gttaacgcca tcaatgatct tccggattat atgaagctct    1200
gcttcctagc tctctacaac actatcaatg agatagctta tgacaatctg aaggacaagg    1260
gggaaaacat tcttccatac ctaacaaaag cgtgggcaga tttatgcaat gcattcctac    1320
aagaagcaaa atggctgtac aataagtcca caccaacatt tgatgactat ttcggaaatg    1380
catggaaatc atcctcaggg cctcttcaac taatttttgc ctactttgcc gtggttcaaa    1440
acatcaagaa agaggaaatt gaaaacttac aaaagtatca tgatatcatc agtaggcctt    1500
cccacatctt tcgtctttgc aacgacctgg cttcagcatc ggctgagata gcgagaggtg    1560
aaactgcgaa ttccgtatcc tgctacatgc gtacaaaagg catttctgag gaacttgcta    1620
ctgaatccgt aatgaatttg atcgacgaaa cctgtaaaaa gatgaacaaa gaaaagcttg    1680
gtggctcttt gtttgcaaaa ccttttgtcg aaacagctat taaccttgca cggcaatccc    1740
attgcactta tcataacgga gatgcgcata cttcaccaga cgagctaact aggaaacgtg    1800
tcctgtcagt aatcacagag cctattctac cctttgagag ataaaagtaa caggttttcc    1860
atgttgtcgt ctgcaagaac aaataacata tgctgcgtag aaaattaagc catgtaaata    1920
ggctttaact ccatgtccgg cggagttttt gcagcagcaa gtaccctcct gtattgtgga    1980
tggagagtat tgtatatttt cattcagatt acaaggaaga ttatatatcc attttcttat    2040
tttgagtgca aaaaaaaaaa aa                                             2062
```

<210> SEQ ID NO 5
<211> LENGTH: 595
<212> TYPE: PRT
<213> ORGANISM: Artificial Sequence
<220> FEATURE:
<223> OTHER INFORMATION: Populus alba x Populus tremula isoprene
      synthase sequence

<400> SEQUENCE: 5

-continued

```
Met Ala Thr Glu Leu Leu Cys Leu His Arg Pro Ile Ser Leu Thr His
 1               5                  10                 15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Ala Arg Arg Ser Ala Asn Tyr Glu Pro Asn Ser
 50                  55                  60

Trp Asp Tyr Asp Phe Leu Leu Ser Ser Asp Thr Asp Glu Ser Ile Glu
 65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Leu Glu Leu Ile Asp
                100                 105                 110

Asn Val Gln Arg Leu Gly Leu Gly Tyr Arg Phe Glu Ser Asp Ile Arg
            115                 120                 125

Arg Ala Leu Asp Arg Phe Val Ser Ser Gly Gly Phe Asp Gly Val Thr
        130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Thr Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Arg Val Phe Ala Ile Ser His Leu Lys Glu Leu Ser Glu
        210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
                260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Lys Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
    370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
```

```
                420             425             430
Pro Thr Phe Asp Asp Tyr Phe Gly Asn Ala Trp Lys Ser Ser Gly
            435             440             445

Pro Leu Gln Leu Ile Phe Ala Tyr Phe Ala Val Val Gln Asn Ile Lys
        450                 455             460

Lys Glu Glu Ile Glu Asn Leu Gln Lys Tyr His Asp Ile Ile Ser Arg
465             470              475             480

Pro Ser His Ile Phe Arg Leu Cys Asn Asp Leu Ala Ser Ala Ser Ala
                485             490             495

Glu Ile Ala Arg Gly Glu Thr Ala Asn Ser Val Ser Cys Tyr Met Arg
            500             505             510

Thr Lys Gly Ile Ser Glu Glu Leu Ala Thr Glu Ser Val Met Asn Leu
            515             520             525

Ile Asp Glu Thr Cys Lys Lys Met Asn Lys Glu Lys Leu Gly Gly Ser
            530             535             540

Leu Phe Ala Lys Pro Phe Val Glu Thr Ala Ile Asn Leu Ala Arg Gln
545             550             555             560

Ser His Cys Thr Tyr His Asn Gly Asp Ala His Thr Ser Pro Asp Glu
                565             570             575

Leu Thr Arg Lys Arg Val Leu Ser Val Ile Thr Glu Pro Ile Leu Pro
            580             585             590

Phe Glu Arg
        595

<210> SEQ ID NO 6
<211> LENGTH: 2062
<212> TYPE: DNA
<213> ORGANISM: Artificial Sequence
<220> FEATURE:
<223> OTHER INFORMATION: Populus alba x Populus tremula isoprene
      synthase mRNA translated

<400> SEQUENCE: 6
gcgccggcgc agctgctctc tctcttttag gacgacgtca aaggtaatga tctccgtacc      60
gttgacttaa taacacgaac gtggcaggtt agagtgactg tgtgtttgac aagtctttag     120
ggaatggatt tcagtaggtc cggtgaggga attgaaactt tgagtctaca agacattcgt     180
gtcttttgca gtcgaagtgt cttttgtcttt gtcttcggtc tgccagacgg ttaatacttg     240
gtttatcgac cctaatacta aaaaacgaca gaagtctgtg actgcttagc taacttcata     300
tgtttctgtt ccgttttttc gacctccgac tccactcttc tctctaattg ttacttttcc     360
gtctcaaaaa ctgagacgaa cttgactatc tattacaggt ttccaatcct aacccaatgg     420
ccaagctctc actgtattcc tctcgggagc tgtctaaaca aagaagtcct cctaaactac     480
cacaatgttt tgatcggaa gtacgatgac gagaatcgaa gtccgaagag tctgtcgtac     540
cgaaactcca gagagttctt cgcaagtcac ctaagttcct agttttaccg ttaaagaacc     600
ttttggaatt cctcctgtgg ttccgttatg attcggatat acttcgaagt aaagaacgta     660
atcttcctct tttatagaac ctactccggt cccacaaacg ttatagtgta gattttctcg     720
agtcgcttct tttctaacct tttctcgacc ggcttgtcca cttagtacgt aacctcgaag     780
gtaacgtagc gtcctgcgtt tctgatcttc gacaaacctc ataacttcgt atggcatttt     840
tccttctacg tttagttcat gacgatcttg aacgatataa cctgatgttg tactaagtta     900
gtcatatggt ttctctagaa gcgctctgta gttccaccac ctccgctcac ccagaacgtt     960
gtttcaacgt aaaacgatttc tgtccaatt aactttcgaa aatgaccgt caacctcaac    1020
```

-continued

```
gcaagcttgg agttatgtca ctaacggcat taagtcatcg tttttacaaa agtaaacatt    1080
gttagtaact actatagata ctacaaatac catgagacct actcgacctc gataaatgtc    1140
tacgacaact ctctacccta caattgcggt agttactaga aggcctaata tacttcgaga    1200
cgaaggatcg agagatgttg tgatagttac tctatcgaat actgttagac ttcctgttcc    1260
ccctttttgta agaaggtatg gattgttttc gcacccgtct aaatacgtta cgtaaggatg    1320
ttcttcgttt taccgacatg ttattcaggt gtggttgtaa actactgata aagcctttac    1380
gtacctttag taggagtccc ggagaagttg attaaaaacg gatgaaacgg caccaagttt    1440
tgtagttctt tctcctttaa cttttgaatg ttttcatagt actatagtag tcatccggaa    1500
gggtgtagaa agcagaaacg ttgctggacc gaagtcgtag ccgactctat cgctctccac    1560
tttgacgctt aaggcatagg acgatgtacg catgttttcc gtaaagactc cttgaacgat    1620
gacttaggca ttacttaaac tagctgcttt ggacattttt ctacttgttt cttttcgaac    1680
caccgagaaa caaacgtttt ggaaaacagc tttgtcgata attggaacgt gccgttaggg    1740
taacgtgaat agtattgcct ctacgcgtat gaagtggtct gctcgattga tcctttgcac    1800
aggacagtca ttagtgtctc ggataagatg ggaaactctc tattttcatt gtccaaaagg    1860
tacaacagca gacgttcttg tttattgtat acgacgcatc ttttaattcg gtacatttat    1920
ccgaaattga ggtacaggcc gcctcaaaaa cgtcgtcgtt catgggagga cataacacct    1980
acctctcata acatataaaa gtaagtctaa tgttccttct aatatatagg taaaagaata    2040
aaactcacgt ttttttttttt tt                                             2062
```

<210> SEQ ID NO 7
<211> LENGTH: 595
<212> TYPE: PRT
<213> ORGANISM: Populus canescens

<400> SEQUENCE: 7

```
Met Ala Thr Glu Leu Leu Cys Leu His Arg Pro Ile Ser Leu Thr His
  1               5                  10                  15

Lys Leu Phe Arg Asn Pro Leu Pro Lys Val Ile Gln Ala Thr Pro Leu
             20                  25                  30

Thr Leu Lys Leu Arg Cys Ser Val Ser Thr Glu Asn Val Ser Phe Thr
         35                  40                  45

Glu Thr Glu Thr Glu Ala Arg Arg Ser Ala Asn Tyr Glu Pro Asn Ser
     50                  55                  60

Trp Asp Tyr Asp Phe Leu Leu Ser Ser Asp Thr Asp Glu Ser Ile Glu
 65                  70                  75                  80

Val Tyr Lys Asp Lys Ala Lys Lys Leu Glu Ala Glu Val Arg Arg Glu
                 85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Gly Val Thr
    130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Thr Lys Ala Ile Leu
            180                 185                 190
```

Ser Leu Tyr Glu Ala Ser Phe Leu Ala Leu Glu Gly Glu Asn Ile Leu
    195                 200                 205

Asp Glu Ala Arg Val Phe Ala Ile Ser His Leu Lys Glu Leu Ser Glu
210                 215                 220

Glu Lys Ile Gly Lys Glu Leu Ala Glu Gln Val Asn His Ala Leu Glu
225                 230                 235                 240

Leu Pro Leu His Arg Thr Gln Arg Leu Glu Ala Val Trp Ser Ile
            245                 250                 255

Glu Ala Tyr Arg Lys Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Lys Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
            420                 425                 430

Pro Thr Phe Asp Asp Tyr Phe Gly Asn Ala Trp Lys Ser Ser Ser Gly
        435                 440                 445

Pro Leu Gln Leu Ile Phe Ala Tyr Phe Ala Val Val Gln Asn Ile Lys
    450                 455                 460

Lys Glu Glu Ile Glu Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
            500                 505                 510

Thr Lys Gly Ile Ser Glu Glu Leu Ala Thr Glu Ser Val Met Asn Leu
        515                 520                 525

Ile Asp Glu Thr Cys Lys Lys Met Asn Lys Glu Lys Leu Gly Gly Ser
    530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
    595

<210> SEQ ID NO 8

<211> LENGTH: 595
<212> TYPE: PRT
<213> ORGANISM: Populus tremuloides

<400> SEQUENCE: 8

```
Met Ala Thr Glu Leu Leu Cys Leu His Arg Pro Ile Ser Leu Thr His
 1               5                  10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Ser
        35                  40                  45

Glu Thr Glu Thr Glu Thr Arg Arg Ser Ala Asn Tyr Glu Pro Asn Ser
    50                  55                  60

Trp Asp Tyr Asp Tyr Leu Leu Ser Ser Asp Thr Asp Glu Ser Ile Glu
65                  70                  75                  80

Val His Lys Asp Lys Ala Lys Lys Leu Glu Ala Glu Val Arg Arg Glu
                85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Gly Val Thr
    130                 135                 140

Lys Thr Ser Leu His Gly Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Glu Leu Ala Glu Gln Val Ser His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
    370                 375                 380

Ala Leu Tyr Asn Thr Ile Asn Glu Ile Ala Tyr Asp Asn Leu Lys Asp
385                 390                 395                 400
```

```
Lys Gly Glu Asn Ile Leu Pro Tyr Leu Thr Lys Ala Trp Ala Asp Leu
            405                 410                 415
Cys Asn Ala Phe Leu Gln Glu Ala Lys Trp Leu Tyr Asn Lys Ser Thr
        420                 425                 430
Pro Thr Phe Asp Asp Tyr Phe Gly Asn Ala Trp Lys Ser Ser Ser Gly
        435                 440                 445
Pro Leu Gln Leu Ile Phe Ala Tyr Phe Ala Val Val Gln Asn Ile Lys
    450                 455                 460
Lys Glu Glu Ile Glu Asn Leu Gln Lys Tyr His Asp Ile Ile Ser Arg
465                 470                 475                 480
Pro Ser His Ile Phe Arg Leu Cys Asn Asp Leu Ala Ser Ala Ser Ala
                485                 490                 495
Glu Ile Ala Arg Gly Glu Thr Ala Asn Ser Val Ser Cys Tyr Met Arg
                500                 505                 510
Thr Lys Gly Ile Ser Glu Glu Leu Ala Thr Glu Ser Val Met Asn Leu
            515                 520                 525
Ile Asp Glu Thr Trp Lys Lys Met Asn Lys Glu Lys Leu Gly Gly Ser
530                 535                 540
Leu Phe Ala Lys Pro Phe Val Glu Thr Ala Ile Asn Leu Ala Arg Gln
545                 550                 555                 560
Ser His Cys Thr Tyr His Asn Gly Asp Ala His Thr Ser Pro Asp Glu
                565                 570                 575
Leu Thr Arg Lys Arg Val Leu Ser Val Ile Thr Glu Pro Ile Leu Pro
                580                 585                 590
Phe Glu Arg
        595

<210> SEQ ID NO 9
<211> LENGTH: 595
<212> TYPE: PRT
<213> ORGANISM: Populus alba

<400> SEQUENCE: 9

Met Ala Thr Glu Leu Leu Cys Leu His Arg Pro Ile Ser Leu Thr His
1               5                   10                  15
Lys Leu Phe Arg Asn Pro Leu Pro Lys Val Ile Gln Ala Thr Pro Leu
            20                  25                  30
Thr Leu Lys Leu Arg Cys Ser Val Ser Thr Glu Asn Val Ser Phe Thr
        35                  40                  45
Glu Thr Glu Thr Glu Ala Arg Arg Ser Ala Asn Tyr Glu Pro Asn Ser
    50                  55                  60
Trp Asp Tyr Asp Tyr Leu Leu Ser Ser Asp Thr Asp Glu Ser Ile Glu
65                  70                  75                  80
Val Tyr Lys Asp Lys Ala Lys Lys Leu Glu Ala Glu Val Arg Arg Glu
                85                  90                  95
Ile Asn Asn Glu Lys Ala Glu Phe Leu Thr Leu Leu Glu Leu Ile Asp
                100                 105                 110
Asn Val Gln Arg Leu Gly Leu Gly Tyr Arg Phe Glu Ser Asp Ile Arg
            115                 120                 125
Gly Ala Leu Asp Arg Phe Val Ser Ser Gly Gly Phe Asp Ala Val Thr
    130                 135                 140
Lys Thr Ser Leu His Gly Thr Ala Leu Ser Phe Arg Leu Leu Arg Gln
145                 150                 155                 160
His Gly Phe Glu Val Ser Gln Glu Ala Phe Ser Gly Phe Lys Asp Gln
                165                 170                 175
```

```
Asn Gly Asn Phe Leu Glu Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
            195                 200             205

Asp Glu Ala Lys Val Phe Ala Ile Ser His Leu Lys Glu Leu Ser Glu
            210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
                260                 265                 270

Ala Ile Leu Asp Tyr Asn Met Ile Gln Ser Val Tyr Gln Arg Asp Leu
            275                 280                 285

Arg Glu Thr Ser Arg Trp Trp Arg Arg Val Gly Leu Ala Thr Lys Leu
            290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
            355                 360                 365

Val Asn Ala Ile Asn Asp Leu Pro Asp Tyr Met Lys Leu Cys Phe Leu
370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
                420                 425                 430

Pro Thr Phe Asp Asp Tyr Phe Gly Asn Ala Trp Lys Ser Ser Ser Gly
            435                 440                 445

Pro Leu Gln Leu Val Phe Ala Tyr Phe Ala Val Val Gln Asn Ile Lys
            450                 455                 460

Lys Glu Glu Ile Glu Asn Leu Gln Lys Tyr His Asp Thr Ile Ser Arg
465                 470                 475                 480

Pro Ser His Ile Phe Arg Leu Cys Asn Asp Leu Ala Ser Ala Ser Ala
            485                 490                 495

Glu Ile Ala Arg Gly Glu Thr Ala Asn Ser Val Ser Cys Tyr Met Arg
            500                 505                 510

Thr Lys Gly Ile Ser Glu Glu Leu Ala Thr Glu Ser Val Met Asn Leu
            515                 520                 525

Ile Asp Glu Thr Trp Lys Lys Met Asn Lys Glu Lys Leu Gly Gly Ser
            530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
```

595

<210> SEQ ID NO 10
<211> LENGTH: 595
<212> TYPE: PRT
<213> ORGANISM: Populus nigra

<400> SEQUENCE: 10

```
Met Ala Thr Glu Leu Leu Cys Leu His Arg Pro Ile Ser Leu Thr His
  1               5                  10                  15

Lys Leu Phe Arg Asn Pro Leu Pro Lys Val Ile Gln Ala Thr Pro Leu
             20                  25                  30

Thr Leu Lys Leu Arg Cys Ser Val Ser Thr Glu Asn Val Ser Phe Thr
         35                  40                  45

Glu Thr Glu Thr Glu Thr Arg Arg Ser Ala Asn Tyr Glu Pro Asn Ser
     50                  55                  60

Trp Asp Tyr Asp Tyr Leu Leu Ser Ser Asp Thr Asp Glu Ser Ile Glu
 65                  70                  75                  80

Val Tyr Lys Asp Lys Ala Lys Lys Leu Glu Ala Glu Val Arg Arg Glu
                 85                  90                  95

Ile Asn Asn Glu Lys Ala Glu Phe Leu Thr Leu Pro Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Ala Val Thr
    130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Lys Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Asp Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asp Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asp Asp Leu Pro Asp Tyr Met Lys Leu Cys Phe Leu
```

```
                370             375             380
Ala Leu Tyr Asn Thr Ile Asn Glu Ile Ala Tyr Asp Asn Leu Lys Asp
385             390             395             400

Lys Gly Glu Asn Ile Leu Pro Tyr Leu Thr Lys Ala Trp Ala Asp Leu
            405             410             415

Cys Asn Ala Phe Leu Gln Glu Ala Lys Trp Leu Tyr Asn Lys Ser Thr
        420             425             430

Pro Thr Phe Asp Glu Tyr Phe Gly Asn Ala Trp Lys Ser Ser Ser Gly
    435             440             445

Pro Leu Gln Leu Val Phe Ala Tyr Phe Ala Val Val Gln Asn Ile Lys
450             455             460

Lys Glu Glu Ile Asp Asn Leu Gln Lys Tyr His Asp Ile Ile Ser Arg
465             470             475             480

Pro Ser His Ile Phe Arg Leu Cys Asn Asp Leu Ala Ser Ala Ser Ala
            485             490             495

Glu Ile Ala Arg Gly Glu Thr Ala Asn Ser Val Ser Cys Tyr Met Arg
        500             505             510

Thr Lys Gly Ile Ser Glu Glu Leu Ala Thr Glu Ser Val Met Asn Leu
    515             520             525

Ile Asp Glu Thr Trp Lys Lys Met Asn Lys Glu Lys Leu Gly Gly Ser
530             535             540

Leu Phe Ala Lys Pro Phe Val Glu Thr Ala Ile Asn Leu Ala Arg Gln
545             550             555             560

Ser His Cys Thr Tyr His Asn Gly Asp Ala His Thr Ser Pro Asp Glu
            565             570             575

Leu Thr Arg Lys Arg Val Leu Ser Val Ile Thr Glu Pro Ile Leu Pro
        580             585             590

Phe Glu Arg
    595

<210> SEQ ID NO 11
<211> LENGTH: 1916
<212> TYPE: DNA
<213> ORGANISM: Artificial Sequence
<220> FEATURE:
<223> OTHER INFORMATION: synthetic isoprene synthase gene

<400> SEQUENCE: 11
ctgcaggagc tgttgacaat taatcatcga actagtttaa tgtgtggaat tgtgagcgga      60
taacaattaa gcttaggagg aattcttatg ggtcatcacc atcaccatca ccatcacagt     120
ggtgcaactg aattattgtg cttgcaccgt ccaatctcac tgacacacaa actgttccga     180
aatcccttac ctaaagtcat ccaggccact cccttaactt tgaaactccg atgttctgta     240
agcacagaaa acgtcagctt cacagaaaca gaaacagaag cccgacggtc tgccaattat     300
gaaccaaata gctgggatta tgatttttg ctgtcttcag acactgacga atcgattgaa     360
gtatacaaag acaaggccaa aaagctggag gctgaggtgc gacgagagat taacaatgaa     420
aaggcagagt ttttgactct gcttgaactg attgataatg tccaaaggtt aggattgggt     480
taccggttcg agagtgacat taggcgagcc ctcgaccgat tgtttcttc aggaggattt     540 gatggtgtta caaaaactag ccttcatgct actgctctta gcttcaggct tctccgacag     600
catggctttg aggtctctca agaagcgttc agtggattca aggatcaaaa tggcaatttc     660
ttggaaaacc ttaaggagga caccaaggca attctaagcc tatatgaagc ctcatttctt     720
gcattagaag gagaaaatat cttggatgag gccagggtgt ttgcaatttc acatctaaaa     780
```

```
gagctcagcg aagaaaagat tggaaaagag ctggccgaac aggtgaatca tgcattggag    840
cttccattgc atcgcaggac gcaacgacta gaagctgttt ggagtattga agcataccgt    900
aaaaaggaag atgcaaatca agtactgcta gaacttgcta ttttggacta caacatgatt    960
caatcagtat accaacgtga tcttcgtgag acatcaaggt ggtggaggcg agtgggtctt   1020
gcaacaaagt tgcatttgc taaagacagg ttaattgaga cttttactg gcagttgga    1080
gttgcgttcg aacctcaata cagtgattgc cgtaattcag tagcaaaaat gttttcattt   1140
gtaacaatca ttgatgatat ctatgatgtt tatggtactc tggatgagct ggagctattt   1200
acagatgctg ttgagcgatg ggatgttaac gccatcaatg atcttccgga ttatatgaag   1260
ctctgcttcc tagctctcta acactatc aatgagattg cttatgacaa tctgaaggac   1320
aaggggaaa acattcttcc atacctaaca aaagcgtggg cagatttatg caatgcattc   1380
ctacaagaag caaatggct gtacaataag tccacaccaa catttgatga ctatttcgga   1440
aatgcatgga atcatcctc agggcctctt caactaattt ttgcctactt tgccgtggtt   1500
caaaacatca agaaagagga aattgaaaac ttacaaaagt atcatgatat catcagtagg   1560
ccttcccaca tctttcgtct ttgcaacgac ctggcttcag catcggctga gattgcacga   1620
ggtgaaactg ccaattccgt atcctgctac atgcgtacaa aaggcatttc tgaggaactt   1680
gctactgaat ccgtaatgaa tttgatcgac gaaacctgga aaagatgaa caagaaaag    1740
ctcggtggct ctttgttgc aaaaccttt gtcgaaacag ctattaacct tgcacggcaa   1800
tcccattgca cttatcataa cggagatgcg catacttcac cagacgagct aactaggaaa   1860
cgtgtcctgt cagtaatcac agagcctatt ctacccttg agcgataata ggtacc       1916
```

<210> SEQ ID NO 12
<211> LENGTH: 606
<212> TYPE: PRT
<213> ORGANISM: Artificial Sequence
<220> FEATURE:
<223> OTHER INFORMATION: synthetic isoprene synthase

<400> SEQUENCE: 12

```
Met Gly His His His His His His His Ser Gly Ala Thr Glu Leu
1               5                   10                  15

Leu Cys Leu His Arg Pro Ile Ser Leu Thr His Lys Leu Phe Arg Asn
            20                  25                  30

Pro Leu Pro Lys Val Ile Gln Ala Thr Pro Leu Thr Leu Lys Leu Arg
        35                  40                  45

Cys Ser Val Ser Thr Glu Asn Val Ser Phe Thr Glu Thr Glu Thr Glu
    50                  55                  60

Ala Arg Arg Ser Ala Asn Tyr Glu Pro Asn Ser Trp Asp Tyr Asp Phe
65                  70                  75                  80

Leu Leu Ser Ser Asp Thr Asp Glu Ser Ile Glu Val Tyr Lys Asp Lys
                85                  90                  95

Ala Lys Lys Leu Glu Ala Glu Val Arg Arg Glu Ile Asn Asn Glu Lys
            100                 105                 110

Ala Glu Phe Leu Thr Leu Leu Glu Leu Ile Asp Asn Val Gln Arg Leu
        115                 120                 125

Gly Leu Gly Tyr Arg Phe Glu Ser Asp Ile Arg Arg Ala Leu Asp Arg
    130                 135                 140

Phe Val Ser Ser Gly Gly Phe Asp Gly Val Thr Lys Thr Ser Leu His
145                 150                 155                 160

Ala Thr Ala Leu Ser Phe Arg Leu Leu Arg Gln His Gly Phe Glu Val
                165                 170                 175
```

```
Ser Gln Glu Ala Phe Ser Gly Phe Lys Asp Gln Asn Gly Asn Phe Leu
        180                 185                 190
Glu Asn Leu Lys Glu Asp Thr Lys Ala Ile Leu Ser Leu Tyr Glu Ala
        195                 200                 205
Ser Phe Leu Ala Leu Glu Gly Glu Asn Ile Leu Asp Glu Ala Arg Val
210                 215                 220
Phe Ala Ile Ser His Leu Lys Glu Leu Ser Glu Lys Ile Gly Lys
225                 230                 235                 240
Glu Leu Ala Glu Gln Val Asn His Ala Leu Glu Leu Pro Leu His Arg
                    245                 250                 255
Arg Thr Gln Arg Leu Glu Ala Val Trp Ser Ile Glu Ala Tyr Arg Lys
                    260                 265                 270
Lys Glu Asp Ala Asn Gln Val Leu Leu Glu Leu Ala Ile Leu Asp Tyr
                    275                 280                 285
Asn Met Ile Gln Ser Val Tyr Gln Arg Asp Leu Arg Glu Thr Ser Arg
        290                 295                 300
Trp Trp Arg Arg Val Gly Leu Ala Thr Lys Leu His Phe Ala Lys Asp
305                 310                 315                 320
Arg Leu Ile Glu Ser Phe Tyr Trp Ala Val Gly Val Ala Phe Glu Pro
                    325                 330                 335
Gln Tyr Ser Asp Cys Arg Asn Ser Val Ala Lys Met Phe Ser Phe Val
                    340                 345                 350
Thr Ile Ile Asp Asp Ile Tyr Asp Val Tyr Gly Thr Leu Asp Glu Leu
                    355                 360                 365
Glu Leu Phe Thr Asp Ala Val Glu Arg Trp Asp Val Asn Ala Ile Asn
        370                 375                 380
Asp Leu Pro Asp Tyr Met Lys Leu Cys Phe Leu Ala Leu Tyr Asn Thr
385                 390                 395                 400
Ile Asn Glu Ile Ala Tyr Asp Asn Leu Lys Asp Lys Gly Glu Asn Ile
                    405                 410                 415
Leu Pro Tyr Leu Thr Lys Ala Trp Ala Asp Leu Cys Asn Ala Phe Leu
                    420                 425                 430
Gln Glu Ala Lys Trp Leu Tyr Asn Lys Ser Thr Pro Thr Phe Asp Asp
        435                 440                 445
Tyr Phe Gly Asn Ala Trp Lys Ser Ser Ser Gly Pro Leu Gln Leu Ile
        450                 455                 460
Phe Ala Tyr Phe Ala Val Val Gln Asn Ile Lys Lys Glu Glu Ile Glu
465                 470                 475                 480
Asn Leu Gln Lys Tyr His Asp Ile Ile Ser Arg Pro Ser His Ile Phe
                    485                 490                 495
Arg Leu Cys Asn Asp Leu Ala Ser Ala Ser Ala Glu Ile Ala Arg Gly
                    500                 505                 510
Glu Thr Ala Asn Ser Val Ser Cys Tyr Met Arg Thr Lys Gly Ile Ser
        515                 520                 525
Glu Glu Leu Ala Thr Glu Ser Val Met Asn Leu Ile Asp Glu Thr Trp
        530                 535                 540
Lys Lys Met Asn Lys Glu Lys Leu Gly Gly Ser Leu Phe Ala Lys Pro
545                 550                 555                 560
Phe Val Glu Thr Ala Ile Asn Leu Ala Arg Gln Ser His Cys Thr Tyr
                    565                 570                 575
His Asn Gly Asp Ala His Thr Ser Pro Asp Glu Leu Thr Arg Lys Arg
                    580                 585                 590
Val Leu Ser Val Ile Thr Glu Pro Ile Leu Pro Phe Glu Arg
```

<210> SEQ ID NO 13
<211> LENGTH: 1462
<212> TYPE: DNA
<213> ORGANISM: Artificial Sequence
<220> FEATURE:
<223> OTHER INFORMATION: synthetic isoprene synthase gene

<400> SEQUENCE: 13

```
ttttggaatt cctcctgtgg ttccgttatg attcggatat acttcgaagt aaagaacgta      60
tagaaggaga aaatatcttg gatgaggcca gggtgtttgc aatatcacat ctaaaagagc     120
tcagcgaaga aaagattgga aaagagctgg ccgaacaggt gaatcatgca ttggagcttc     180
cattgcatcg caggacgcaa agactagaag ctgtttggag tattgaagca taccgtaaaa     240
aggaagatgc aaatcaagta ctgctagaac ttgctatatt ggactacaac atgattcaat     300
cagtatacca agagatcttc gcgagacat caaggtggtg gaggcgagtg ggtcttgcaa      360
caaagttgca ttttgctaaa gacaggttaa ttgaaagctt ttactgggca gttggagttg     420
cgttcgaacc tcaatacagt gattgccgta attcagtagc aaaaatgttt tcatttgtaa     480
caatcattga tgatatctat gatgtttatg gtactctgga tgagctggag ctatttacag     540
atgctgttga gagatgggat gttaacgcca tcaatgatct tccggattat atgaagctct     600
gcttcctagc tctctacaac actatcaatg agatagctta tgacaatctg aaggacaagg     660
gggaaaacat tcttccatac ctaacaaaag cgtgggcaga tttatgcaat gcattcctac     720
aagaagcaaa atggctgtac aataagtcca caccaacatt tgatgactat ttcggaaatg     780
catggaaatc atcctcaggg cctcttcaac taatttttgc ctactttgcc gtggttcaaa     840
acatcaagaa agaggaaatt gaaaacttac aaaagtatca tgatatcatc agtaggcctt     900
cccacatctt tcgtctttgc aacgacctgg cttcagcatc ggctgagata gcgagaggtg     960
aaactgcgaa ttccgtatcc tgctacatgc gtacaaaagg catttctgag gaacttgcta    1020
ctgaatccgt aatgaatttg atcgacgaaa cctgtaaaaa gatgaacaaa gaaaagcttg    1080
gtggctcttt gtttgcaaaa cctttttgtcg aaacagctat taaccttgca cggcaatccc    1140
attgcactta tcataacgga gatgcgcata cttcaccaga cgagctaact aggaaacgtg    1200
tcctgtcagt aatcacagag cctattctac cctttgagat aaaagtaa caggttttcc       1260
atgttgtcgt ctgcaagaac aaataacata tgctgcgtag aaaattaagc catgtaaata    1320
ggctttaact ccatgtccgg cggagttttt gcagcagcaa gtaccctcct gtattgtgga    1380
tggagagtat tgtatatttt cattcagatt acaaggaaga ttatatatcc attttcttat    1440
tttgagtgca aaaaaaaaa aa                                              1462
```

<210> SEQ ID NO 14
<211> LENGTH: 393
<212> TYPE: PRT
<213> ORGANISM: Artificial Sequence
<220> FEATURE:
<223> OTHER INFORMATION: synthetic isoprene synthase

<400> SEQUENCE: 14

```
Glu Gly Glu Asn Ile Leu Asp Glu Ala Arg Val Phe Ala Ile Ser His
 1               5                  10                  15

Leu Lys Glu Leu Ser Glu Glu Lys Ile Gly Lys Glu Leu Ala Glu Gln
            20                  25                  30

Val Asn His Ala Leu Glu Leu Pro Leu His Arg Arg Thr Gln Arg Leu
        35                  40                  45
```

Glu Ala Val Trp Ser Ile Glu Ala Tyr Arg Lys Lys Glu Asp Ala Asn
 50                  55                  60

Gln Val Leu Leu Glu Leu Ala Ile Leu Asp Tyr Asn Met Ile Gln Ser
 65                  70                  75                  80

Val Tyr Gln Arg Asp Leu Arg Glu Thr Ser Arg Trp Trp Arg Arg Val
             85                  90                  95

Gly Leu Ala Thr Lys Leu His Phe Ala Lys Asp Arg Leu Ile Glu Ser
            100                 105                 110

Phe Tyr Trp Ala Val Gly Val Ala Phe Glu Pro Gln Tyr Ser Asp Cys
            115                 120                 125

Arg Asn Ser Val Ala Lys Met Phe Ser Phe Val Thr Ile Ile Asp Asp
130                 135                 140

Ile Tyr Asp Val Tyr Gly Thr Leu Asp Glu Leu Glu Leu Phe Thr Asp
145                 150                 155                 160

Ala Val Glu Arg Trp Asp Val Asn Ala Ile Asn Asp Leu Pro Asp Tyr
            165                 170                 175

Met Lys Leu Cys Phe Leu Ala Leu Tyr Asn Thr Ile Asn Glu Ile Ala
            180                 185                 190

Tyr Asp Asn Leu Lys Asp Lys Gly Glu Asn Ile Leu Pro Tyr Leu Thr
            195                 200                 205

Lys Ala Trp Ala Asp Leu Cys Asn Ala Phe Leu Gln Glu Ala Lys Trp
210                 215                 220

Leu Tyr Asn Lys Ser Thr Pro Thr Phe Asp Asp Tyr Phe Gly Asn Ala
225                 230                 235                 240

Trp Lys Ser Ser Ser Gly Pro Leu Gln Leu Ile Phe Ala Tyr Phe Ala
            245                 250                 255

Val Val Gln Asn Ile Lys Lys Glu Glu Ile Glu Asn Leu Gln Lys Tyr
            260                 265                 270

His Asp Ile Ile Ser Arg Pro Ser His Ile Phe Arg Leu Cys Asn Asp
            275                 280                 285

Leu Ala Ser Ala Ser Ala Glu Ile Ala Arg Gly Glu Thr Ala Asn Ser
290                 295                 300

Val Ser Cys Tyr Met Arg Thr Lys Gly Ile Ser Glu Glu Leu Ala Thr
305                 310                 315                 320

Glu Ser Val Met Asn Leu Ile Asp Glu Thr Cys Lys Lys Met Asn Lys
            325                 330                 335

Glu Lys Leu Gly Gly Ser Leu Phe Ala Lys Pro Phe Val Glu Thr Ala
            340                 345                 350

Ile Asn Leu Ala Arg Gln Ser His Cys Thr Tyr His Asn Gly Asp Ala
            355                 360                 365

His Thr Ser Pro Asp Glu Leu Thr Arg Lys Arg Val Leu Ser Val Ile
            370                 375                 380

Thr Glu Pro Ile Leu Pro Phe Glu Arg
385                 390

<210> SEQ ID NO 15
<211> LENGTH: 1402
<212> TYPE: DNA
<213> ORGANISM: Artificial Sequence
<220> FEATURE:
<223> OTHER INFORMATION: synthetic isoprene synthase gene complement
      sequence

<400> SEQUENCE: 15
atcttcctct tttatagaac ctactccggt cccacaaacg ttatagtgta gattttctcg    60

| | |
|---|---|
| agtcgcttct tttctaacct tttctcgacc ggcttgtcca cttagtacgt aacctcgaag | 120 |
| gtaacgtagc gtcctgcgtt tctgatcttc gacaaacctc ataacttcgt atggcatttt | 180 |
| tccttctacg tttagttcat gacgatcttg aacgatataa cctgatgttg tactaagtta | 240 |
| gtcatatggt ttctctagaa gcgctctgta gttccaccac ctccgctcac ccagaacgtt | 300 |
| gtttcaacgt aaaacgattt ctgtccaatt aactttcgaa aatgaccegt caacctcaac | 360 |
| gcaagcttgg agttatgtca ctaacggcat taagtcatcg ttttacaaa agtaaacatt | 420 |
| gttagtaact actatagata ctacaaatac catgagacct actcgacctc gataaatgtc | 480 |
| tacgacaact ctctacccta caattgcggt agttactaga aggcctaata tacttcgaga | 540 |
| cgaaggatcg agagatgttg tgatagttac tctatcgaat actgttagac ttcctgttcc | 600 |
| cccttttgta agaaggtatg gattgttttc gcacccgtct aaatacgtta cgtaaggatg | 660 |
| ttcttcgttt taccgacatg ttattcaggt gtggttgtaa actactgata aagcctttac | 720 |
| gtacctttag taggagtccc ggagaagttg attaaaaacg gatgaaacgg caccaagttt | 780 |
| tgtagttctt tctcctttaa cttttgaatg ttttcatagt actatagtag tcatccggaa | 840 |
| gggtgtagaa agcagaaacg ttgctggacc gaagtcgtag ccgactctat cgctctccac | 900 |
| tttgacgctt aaggcatagg acgatgtacg catgttttcc gtaaagactc cttgaacgat | 960 |
| gacttaggca ttacttaaac tagctgcttt ggacatttt ctacttgttt cttttcgaac | 1020 |
| caccgagaaa caaacgtttt ggaaaacagc tttgtcgata attggaacgt gccgttaggg | 1080 |
| taacgtgaat agtattgcct ctacgcgtat gaagtggtct gctcgattga tcctttgcac | 1140 |
| aggacagtca ttagtgtctc ggataagatg ggaaactctc tattttcatt gtccaaaagg | 1200 |
| tacaacagca gacgttcttg tttattgtat acgacgcatc ttttaattcg gtacatttat | 1260 |
| ccgaaattga ggtacaggcc gcctcaaaaa cgtcgtcgtt catgggagga cataacacct | 1320 |
| acctctcata acatataaaa gtaagtctaa tgttccttct aatatatagg taaaagaata | 1380 |
| aaactcacgt tttttttt tt | 1402 |

<210> SEQ ID NO 16
<211> LENGTH: 1788
<212> TYPE: DNA
<213> ORGANISM: Artificial Sequence
<220> FEATURE:
<223> OTHER INFORMATION: synthetic isoprene synthase gene

<400> SEQUENCE: 16

| | |
|---|---|
| atggcaactg aattattgtg cttgcaccgt ccaatctcac tgacacacaa actgttccga | 60 |
| aatcccttac ctaaagtcat ccaggccact cccttaactt tgaaactccg atgttctgta | 120 |
| agcacagaaa acgtcagctt cacagaaaca gaaacagaag cccgacggtc tgccaattat | 180 |
| gaaccaaata gctgggatta tgattttttg ctgtcttcag acactgacga atcgattgaa | 240 |
| gtatacaaag acaaggccaa aaagctggag gctgaggtgc gacgagagat taacaatgaa | 300 |
| aaggcagagt ttttgactct gcttgaactg attgataatg tccaaaggtt aggattgggt | 360 |
| taccggttcg agagtgacat taggcgagcc ctcgaccgat tgtttcttc aggaggattt | 420 |
| gatggtgtta caaaaactag ccttcatgct actgctctta gcttcaggct tctccgacag | 480 |
| catggctttg aggtctctca agaagcgttc agtggattca aggatcaaaa tggcaatttc | 540 |
| ttggaaaacc ttaaggagga caccaaggca attctaagcc tatatgaagc tcatttctct | 600 |
| gcattagaag gagaaaatat cttggatgag gccagggtgt ttgcaatttc acatctaaaa | 660 |
| gagctcagcg aagaaaagat tggaaaagag ctggccgaac aggtgaatca tgcattggag | 720 |

-continued

```
cttccattgc atcgcaggac gcaacgacta gaagctgttt ggagtattga agcataccgt    780
aaaaaggaag atgcaaatca agtactgcta gaacttgcta ttttggacta caacatgatt    840
caatcagtat accaacgtga tcttcgtgag acatcaaggt ggtggaggcg agtgggtctt    900
gcaacaaagt tgcattttgc taaagacagg ttaattgaga gcttttactg ggcagttgga    960
gttgcgttcg aacctcaata cagtgattgc cgtaattcag tagcaaaaat gttttcattt   1020
gtaacaatca ttgatgatat ctatgatgtt tatggtactc tggatgagct ggagctattt   1080
acagatgctg ttgagcgatg ggatgttaac gccatcaatg atcttccgga ttatatgaag   1140
ctctgcttcc tagctctcta caacactatc aatgagattg cttatgacaa tctgaaggac   1200 aaggggggaaa acattcttcc atacctaaca aaagcgtggg cagatttatg caatgcattc   1260
ctacaagaag caaaatggct gtacaataag tccacaccaa catttgatga ctatttcgga   1320
aatgcatgga aatcatcctc agggcctctt caactaattt ttgcctactt tgccgtggtt   1380
caaaacatca agaaagagga aattgaaaac ttacaaaagt atcatgatat catcagtagg   1440
ccttcccaca tctttcgtct ttgcaacgac ctggcttcag catcggctga gattgcacga   1500
ggtgaaactg ccaattccgt atcctgctac atgcgtacaa aaggcatttc tgaggaactt   1560
gctactgaat ccgtaatgaa tttgatcgac gaaacctgga aaaagatgaa caaagaaaag   1620
ctcggtggct ctttgtttgc aaaaccttt  gtcgaaacag ctattaacct tgcacggcaa   1680
tcccattgca cttatcataa cggagatgcg catacttcac cagacgagct aactaggaaa   1740
cgtgtcctgt cagtaatcac agagcctatt ctacctttg agcgataa                 1788
```

What is claimed is:

1. A method for the production of isoprene, the method comprising:
culturing a genetically engineered cyanobacterium comprising a nucleic acid encoding a plant isoprene synthase in a bioreactor to produce isoprene, said nucleic acid comprising a sequence that has at least 90% identity to the nucleic acid sequence of SEQ ID NO: 16, wherein said bioreactor contains a water immiscible organic solvent, and the isoprene is trapped in said solvent.

2. The method of claim 1, wherein said gene is codon-optimized to express said synthase in said cyanobacterium.

3. The method of claim 1, wherein said cyanobacterium is of a genus selected from the group consisting of: *Chamaesiphon, Chroococcus, Cyanobacterium, Cyanobium, Cyanothece, Dactylococcopsis, Gloeobacter, Gloeocapsa, Gloeothece, Microcystis, Prochlorococcus, Prochloron, Synechococcus, Cyanocystis, Dermocarpella, Stanieria, Xenococcus, Chroococcidiopsis, Myxosarcina, Pleurocapsa, Arthrospira, Borzia, Crinalium, Geitlerinema, Leptolyngbya, Limnothrix, Lyngbya, Microcoleus, Oscillatoria, Planktothrix, Prochlorothrix, Pseudanabaena, Spirulina, Starria, Symploca, Trichodesmium, Tychonema, Anabaena, Anabaenopsis, Aphanizomenon, Calothrix, Cyanospira, Cylindrospermopsis, Cylindrospermum, Nodularia, Nostoc, Rivularia, Scytonema, Tolypothrix, Chlorogloeopsis, Fischerella, Geitleria, Iyengariella, Nostochopsis*, and *Stigonema*.

4. The method of claim 1, wherein said cyanobacterium is a thermophilic cyanobacterium.

5. The method of claim 1, wherein said cyanobacterium is *Thermosynechococcus elongates* BP1, *Anabaena* 7120, or *Synechocystis* sp. PCC 6803.

6. The method of claim 1, wherein said cyanobacterium produces isoprene when cultured in the presence of carbon dioxide.

7. The method of claim 1, wherein said cyanobacterium produces said isoprene from precursors generated via the 2-C-methyl-D-erythritol-4-phosphate metabolic pathway.

8. The method of claim 1, wherein said nucleic acid comprises a sequence that has at least 95% identity to the nucleic acid sequence of SEQ ID NO: 16.

9. The method of claim 1, wherein said gene comprises the nucleic acid sequence of SEQ ID NO: 16.

10. The method of claim 1, further comprising collecting said isoprene from the organic solvent.

11. A method for the production of isoprene, the method comprising: culturing a cyanobacterium comprising an exogenous nucleic acid that comprises a sequence at least 90% identical to SEQ ID NO:15 in a bioreactor under conditions in which the nucleic acid is expressed and the cyanobacterium produces isoprene.

12. The method of claim 11, wherein said cyanobacterium is of a genus selected from the group consisting of: *Chamaesiphon, Chroococcus, Cyanobacterium, Cyanobium, Cyanothece, Dactylococcopsis, Gloeobacter, Gloeocapsa, Gloeothece, Microcystis, Prochlorococcus, Prochloron, Synechococcus, Cyanocystis, Dermocarpella, Stanieria, Xenococcus, Chroococcidiopsis, Myxosarcina, Pleurocapsa, Arthrospira, Borzia, Crinalium, Geitlerinema, Halospirulina, Leptolyngbya, Limnothrix, Lyngbya, Microcoleus, Oscillatoria, Planktothrix, Prochlorothrix, Pseudanabaena, Spirulina, Starria, Symploca, Trichodesmium, Tychonema, Anabaena, Anabaenopsis, Aphanizomenon, Calothrix, Cyanospira, Cylindrospermopsis, Cylindrospermum, Nodularia, Nostoc, Rivularia, Scytonema, Tolypothrix, Chlorogloeopsis, Fischerella, Geitleria, Iyengariella, Nostochopsis*, and *Stigonema*.

13. The method of claim 11, wherein said cyanobacterium is a thermophilic cyanobacterium.

14. The method of claim 11, wherein said cyanobacterium is *Thermosynechococcus elongatus* BP1, Anabaena 7120, or *Synechocystis* sp. PCC 6803.

15. The method of claim 11, wherein said cyanobacterium produces isoprene when cultured in the presence of carbon dioxide.

16. The method of claim 11, wherein said cyanobacterium produces said isoprene from precursors generated via the 2-C-methyl-D-erythritol-4-phosphate metabolic pathway.

17. The method of claim 11, wherein said nucleic acid comprises SEQ ID NO:15.

18. The method of claim 11, wherein said exogenous nucleic acid comprises a sequence at least 95% identical to SEQ ID NO:15.

* * * * *